United States Patent
Ji et al.

(10) Patent No.: US 11,942,599 B2
(45) Date of Patent: Mar. 26, 2024

(54) SYMMETRICAL OR ASYMMETRICAL ALKYLSULFONYL IMIDE OR CYCLIC ALKYLENE SULFONYLIMIDE SALTS AS CATHODE ADDITIVES, ELECTROLYTE ADDITIVES, OR SI ANODE ADDITIVES FOR SI ANODE-BASED LI-ION CELLS

(71) Applicant: Enevate Corporation, Irvine, CA (US)

(72) Inventors: Liwen Ji, Irvine, CA (US); Benjamin Park, Irvine, CA (US)

(73) Assignee: Enevate Corporation, Irvine, CA (US)

( * ) Notice: Subject to any disclaimer, the term of this patent is extended or adjusted under 35 U.S.C. 154(b) by 0 days.

(21) Appl. No.: 17/508,348

(22) Filed: Oct. 22, 2021

(65) Prior Publication Data

US 2022/0131193 A1 Apr. 28, 2022

Related U.S. Application Data

(60) Provisional application No. 63/106,718, filed on Oct. 28, 2020.

(51) Int. Cl.
| | | |
|---|---|---|
| *H01M 10/0525* | (2010.01) | |
| *C07C 317/28* | (2006.01) | |
| *H01M 4/38* | (2006.01) | |
| *H01M 10/0567* | (2010.01) | |
| *H01M 10/0569* | (2010.01) | |

(52) U.S. Cl.
CPC ....... *H01M 10/0567* (2013.01); *C07C 317/28* (2013.01); *H01M 4/386* (2013.01); *H01M 10/0525* (2013.01); *H01M 10/0569* (2013.01); *H01M 2300/0028* (2013.01)

(58) Field of Classification Search
CPC ......... H01M 10/0567; H01M 10/0525; H01M 10/0569; H01M 4/386; H01M 2300/0028
See application file for complete search history.

(56) References Cited

U.S. PATENT DOCUMENTS

| | | | |
|---|---|---|---|
| 2002/0081496 A1* | 6/2002 | Tsujioka | ................. C07F 5/022 429/324 |
| 2009/0155686 A1* | 6/2009 | Takezawa | ............. H01M 4/133 429/213 |
| 2011/0027635 A1 | 2/2011 | Muraoka et al. | |
| 2016/0240841 A1* | 8/2016 | He | ........................ H01M 4/625 |

(Continued)

OTHER PUBLICATIONS

International Search Report, PCT/US21/56501, dated Jan. 21, 2022, 14 pages.

(Continued)

*Primary Examiner* — Osei K Amponsah
(74) *Attorney, Agent, or Firm* — McAndrews, Held & Malloy, Ltd.

(57) ABSTRACT

Electrode or electrolyte additives for energy storage devices comprising symmetrical or asymmetrical alkylsulfonyl imide or cyclic alkylene sulfonylimide salts are disclosed. The energy storage device comprises a first electrode and a second electrode, wherein at least one of the first electrode and the second electrode is a Si-based electrode, a separator between the first electrode and the second electrode, and an electrolyte composition. Symmetrical or asymmetrical alkylsulfonyl imide or cyclic alkylene sulfonylimide salts may serve as additives to the electrodes or to the electrolyte composition, or both.

19 Claims, 19 Drawing Sheets

(56) References Cited

U.S. PATENT DOCUMENTS

2016/0329560 A1     11/2016   Young et al.
2018/0251681 A1*   9/2018   Zhang .............. H01M 10/0567

OTHER PUBLICATIONS

Murmann et al., Lithium-Cyclo-Difluoromethane-1,1-bis-(sulfonyl)imide as a Stabilizing Electrolyte Additive for Improved High Voltage Applications in Lithium-ion Batteries, Physical Chemistry Chemical Physics, vol. 17, 2015, 7 pages.

Qiang Ma et al., Impact of Anionic Structure of Lithium Salt on the Cycling Stability of Lithium-Metal Anode in Li-S Batteries, Journal of The Electrochemical Society, vol. 163(8), 2016, pp. A1776-A1783.

Fang et al., Novel Concentrated Li[(FSO2)(n-C4F9SO2)N]-Based Ether Electrolyte for Superior Stability of Metallic Lithium Anode, Applied Materials & Interfaces, 2016, 8 pages.

Tong et al., The Salt Matters: Enhanced Reversibility of Li-O2 Batteries with a Li[(DF3SO2)(n-C4F9SO2)N]-Based Electrolyte, Advanced Materials, 2017, 6 pages.

Deng et al., Lithium (Fluorosulfonyl( (Pentafluorethylsulfonyl)imide/poly (ethylene oxide) Polymer Electrolyte: Physical and Electrochemical Properties, Solid State Ionics, vol. 338, 2019, pp. 161-167.

Xiao et al., New Lithium Salt Forms Interphases Suppressing Both Li Dendrite and Polysulfide Shuttling, vol. 338, 2019, pp. 161-167.

Ahmed et al., Highly Conductive Divalent Fluorosulfonyl imide Based Electrolytes Improving Li-ion Battery Performance: Additive Potentiating Electrolytes Action, Journal of Power Sources, vol. 455, 2020, 10 pages.

International Preliminary Report on Patentabiltiy, PCT/US2021/656501, dated May 11, 2023, 9 pages.

* cited by examiner

SYMMETRICAL OR ASYMMETRICAL ALKYLSULFONYL IMIDE OR CYCLIC ALKYLENE SULFONYLIMIDE SALTS AS CATHODE ADDITIVES, ELECTROLYTE ADDITIVES, OR SI ANODE ADDITIVES FOR SI ANODE-BASED LI-ION CELLS

CROSS-REFERENCE TO RELATED APPLICATIONS

This application claims the benefit of U.S. Provisional Application No. 63/106,718, filed Oct. 28, 2020. The entirety of the above referenced application is hereby incorporated by reference.

FIELD

The present application relates generally to electrodes and electrolytes for energy storage devices such as batteries. In particular, the present application relates to electrolytes and additives for use in lithium-ion energy storage devices with silicon-based anode materials.

BACKGROUND

Conventional approaches for battery electrodes and electrolytes may be costly, cumbersome, and/or inefficient—e.g., they may be complex and/or time consuming to implement, and may limit battery lifetime.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method for using symmetrical or asymmetrical alkylsulfonyl imide or cyclic alkylene sulfonylimide salts as electrode and/or electrolyte additives for use in lithium-ion energy storage devices with silicon-based electrode materials, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

FIG. 3A is a flow diagram of a coating process for fabricating a cell with a silicon-dominant electrode. FIG. 3B is a flow diagram for an alternative process for lamination of electrodes.

DETAILED DESCRIPTION

Figure 1:
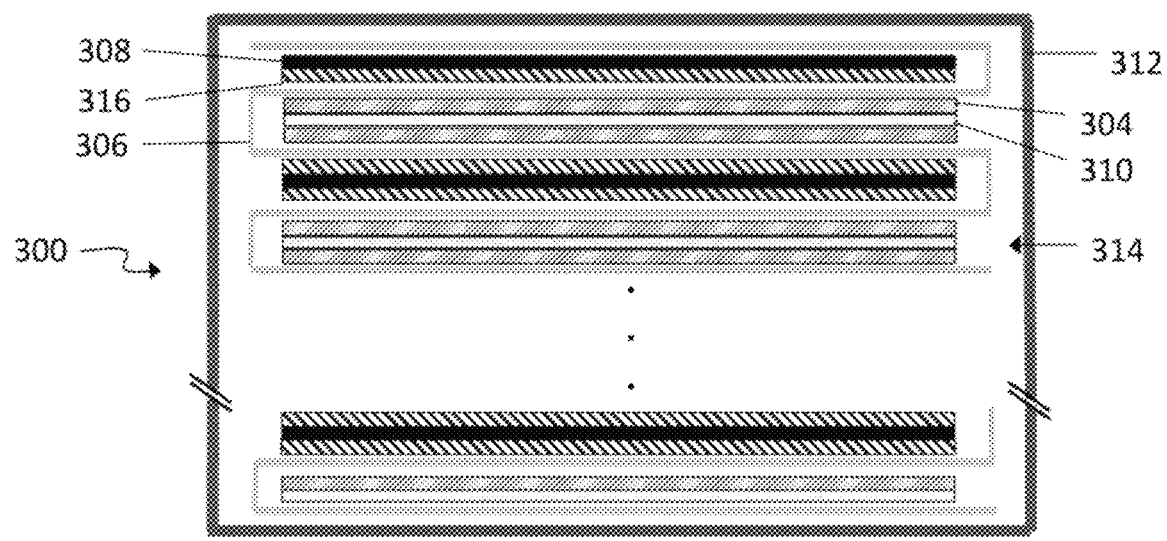
FIG. 1 is a cross-sectional schematic diagram of an example of a lithium ion battery, in accordance with an example embodiment of the disclosure.

As the demands for both zero-emission electric vehicles and grid-based energy storage systems increase, lower costs and improvements in energy density, power density, and safety of lithium (Li)-ion batteries are highly desirable. Enabling the high energy density and safety of Li-ion batteries requires the development of high-capacity, and high-voltage cathodes, high-capacity anodes and accordingly functional electrolytes with high voltage stability, interfacial compatibility with electrodes and safety.

A lithium-ion battery typically includes a separator and/or electrolyte between an anode and a cathode. In one class of batteries, the separator, cathode and anode materials are individually formed into sheets or films. Sheets of the cathode, separator and anode are subsequently stacked or rolled with the separator separating the cathode and anode (e.g., electrodes) to form the battery. Typical electrodes include electro-chemically active material layers on electrically conductive metals (e.g., aluminum and copper). Films can be rolled or cut into pieces which are then layered into stacks. The stacks are of alternating electro-chemically active materials with the separator between them.

Si is one of the most promising anode materials for Li-ion batteries due to its high specific gravimetric and volumetric capacity (3579 mAh/g and 2194 mAh/cm$^3$ vs. 372 mAh/g and 719 mAh/cm$^3$ for graphite), and low lithiation potential (<0.4 V vs. Li/Li$^+$). Among the various cathodes presently available, layered lithium transition-metal oxides such as Ni-rich LiNixCoyMnzO2 (NCM, 0≤x, y, z<1) or LiNi$_x$Co$_y$-Al$_z$O$_2$ (NCA, 0≤x, y, z<1) are promising ones due to their high theoretical capacity (~280 mAh/g) and relatively high average operating potential (3.6 V vs Li/Li$^+$). In addition to Ni-rich NCM or NCA cathode, LiCoO$_2$ (LCO) is also a very attractive cathode material because of its relatively high theoretical specific capacity of 274 mAh g$^{-1}$, high theoretical volumetric capacity of 1363 mAh cm$^{-3}$, low self-discharge, high discharge voltage, and good cycling performance. Coupling Si anodes with high-voltage Ni-rich NCM (or NCA) or LCO cathodes can deliver more energy than conventional Li-ion batteries with graphite-based anodes, due to the high capacity of these new electrodes. However, both Si-based anodes and high-voltage Ni rich NCM (or NCA) or LCO cathodes face formidable technological challenges, and long-term cycling stability with high-Si anodes paired with NCM or NCA cathodes has yet to be achieved.

For anodes, silicon-based materials can provide significant improvement in energy density. However, the large volumetric expansion (>300%) during the Li alloying/dealloying processes can lead to disintegration of the active material and the loss of electrical conduction paths, thereby reducing the cycling life of the battery. In addition, an unstable solid electrolyte interphase (SEI) layer can develop on the surface of the cycled anodes, and leads to an endless exposure of Si particle surfaces to the liquid electrolyte. This results in an irreversible capacity loss at each cycle due to the reduction at the low potential where the liquid electrolyte reacts with the exposed surface of the Si anode. In addition, oxidative instability of the conventional non-aqueous electrolyte takes place at voltages beyond 4.5 V, which can lead to accelerated decay of cycling performance. Because of the generally inferior cycle life of Si compared to graphite, only a small amount of Si or Si alloy is used in conventional anode materials.

The NCM (or NCA) or LCO cathode usually suffers from an inferior stability and a low capacity retention at a high cut-off potential. The reasons can be ascribed to the unstable surface layer's gradual exfoliation, the continuous electrolyte decomposition, and the transition metal ion dissolution into electrolyte solution. The major limitations for LCO cathode are high cost, low thermal stability, and fast capacity fade at high current rates or during deep cycling. LCO cathodes are expensive because of the high cost of Co. Low thermal stability refers to exothermic release of oxygen when a lithium metal oxide cathode is heated. In order to make good use of Si anode//NCM or NCA cathode-, and Si anode//LCO cathode-based Li-ion battery systems, the aforementioned barriers need to be overcome.

One strategy for overcoming these barriers includes exploring new electrolyte additives in order to make good use of Si anode//NCM or NCA cathode-, and Si anode//LCO cathode-based full cells. The next generation of electrolyte additives to be developed should be able to form a uniform, stable SEI layer on the surface of Si anodes. This layer should have low impedance and be electronically insulating, but ionically conductive to Li-ion. Additionally, the SEI layer formed by the additive should have excellent elasticity and mechanical strength to overcome the problem of expansion and shrinkage of the Si anode volume. On the cathode side, the ideal additives should be oxidized preferentially to the solvent molecule in the bare electrolyte, resulting in a protective cathode electrolyte interphase (CEI) film formed on the surface of the Ni-rich NCM (or NCA) and LCO cathodes. At the same time, it should help alleviate the dissolution phenomenon of transition metal ions and decrease surface resistance on cathode side. In addition, they could help improve the physical properties of the electrolyte such as ionic conductivity, viscosity, and wettability.

As discussed above, Li-ion batteries are being intensively pursued in the electric vehicle markets and stationary energy storage devices. To further improve the cell energy density, high-voltage layered transition metal oxide cathodes, examples including Ni-rich (e.g. NCA, NCM), Li-rich cathodes and high capacity and low-voltage anodes, such as Si, Ge, etc may be utilized. However, the performance deterioration of full cells, in which these oxides are paired with a Si or other high capacity anodes, increases markedly at potentials exceeding 4.30 V, limiting their wider use as high-energy cathode materials. Although a higher Ni content provides higher specific capacity for Ni-rich NCM or NCA cathodes, it involves surface instability because the unstable Ni4+ increase during the charging process. As it is favorable to convert the unstable Ni4+ into the more stable Ni3+ or Ni2+, Ni4+ triggers severe electrolyte decomposition at the electrode/electrolyte interface, leading to the reduction of Ni4+ and the oxidative decomposition of the electrolytes. Electrolyte decomposition at the electrolyte/electrode interface causes the accumulation of decomposed adducts on the NCM cathode surface. This hinders Li+ migration between the electrolyte and electrode, which in turn results in the rapid fading of the cycling performance. Thus the practical integration of a silicon anode in Li-ion batteries faces challenges such as large volume changes, an unstable solid-electrolyte interphase, electrolyte drying out, etc.

Attempts for improving the cathode surface properties, such as through-surface coating, surface doping, and use of electrolyte additives that effectively mitigate electrolyte decomposition at the interface, have been attempted. Most of these attempts are based on the cathode-electrolyte interface (CEI) concept, which does not permit electron-transfer reactions, but allows Li+ migration between the electrode and electrolyte.

Another strategy is to develop and utilize specially functionalized film-forming electrolyte additives. The incorporation of a small number of functional additives may help modify the surface chemistry, circumvent the massive volume change and initial capacity loss due to the continuous electrolyte decomposition in high capacity and reactive electrode, such as Si anodes, Ni-rich NCA or NCM cathodes. Suitable reducible or oxidizable electrolyte additives are expected to modify the SEI or CEI interphases, respectively in Li-ion batteries, thus altering and tuning their composition and escorting the corresponding electrochemical properties, such as cycle life, rate capability, energy/power densities, etc. In the present disclosure, symmetrical or asymmetrical alkylsulfonyl imide or cyclic alkylene sulfonylimide metal salts are described for use as additives for different types of cathode-based (such as Ni-rich NCA or NCM, Li-rich, $xLi_2MnO_3 \cdot (1-x)LiNi_aCo_bMn_cO_2$, Li-rich layered oxides, high-voltage spinel oxides, etc.) Li-ion full cells. The symmetrical or asymmetrical alkylsulfonyl imide or cyclic alkylene sulfonylimide metal salts may also be used as electrolyte additives for various electrodes, or as additives for Si anodes. In some embodiments, the additive is a perfluoroalkylsulfonyl imide or acyclic perfluoroalkylene sulfonylimide salt.

The term "alkyl" refers to a straight or branched, saturated, aliphatic radical having the number of carbon atoms indicated. The alkyl moiety may be branched or straight chain. For example, C1-C6 alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 1-11, 1-12 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "fluoro-alkyl" refers to an alkyl group where one, some, or all hydrogen atoms have been replaced by fluorine.

The term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of $-(CH_2)_n-$, where n is 1, 2, 3, 4, 5, 6, 7, 8, 9, or 10. Alkylene groups include, but are not limited to, methylene, ethylene, propylene, isopropylene, butylene, isobutylene, sec-butylene, pentylene and hexylene.

The term "alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group, or substituted with fluorine to form a "fluoro-alkoxy" group.

The term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

The term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

The term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

The term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

The term "cycloalkyl" refers to a saturated or partially unsaturated, monocyclic, fused bicyclic, bridged polycyclic, or spiro ring assembly containing from 3 to 12, from 3 to 10, or from 3 to 7 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, C3-C8 cycloalkyl includes cyclopropyl, cyclobutyl, cyclopentyl, cyclohexyl, cyclooctyl, and norbornane. As used herein, the term "fused" refers to two rings which have two atoms and one bond in common. For example, in the following structure, rings A and B are fused

As used herein, the term "bridged polycyclic" refers to compounds wherein the cycloalkyl contains a linkage of one or more atoms connecting non-adjacent atoms. The following structures

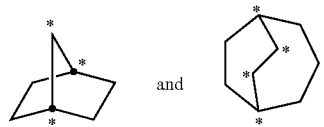 [SMILES: C1C[C@H]2CC[C@H]1C2 ; C1CC2CCC(C1)CC2]

are examples of "bridged" rings. As used herein, the term "spiro" refers to two rings which have one atom in common and the two rings are not linked by a bridge. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl, and norbornanyl; and examples of spiro cycloalkyl groups include spiro[3.3]heptane and spiro[4.5]decane.

The term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

The term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. Aryl groups may include fused multicyclic ring assemblies wherein only one ring in the multicyclic ring assembly is aromatic. Aryl groups can be mono-, di- or tri-substituted by one, two or three radicals. Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

The term "arylene" refers to an aryl group, as defined above, linking at least two other groups. The two moieties linked to the arylene are linked to different atoms of the arylene. Arylene groups include, but are not limited to, phenylene.

The term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. The heteroatoms can also be oxidized, such as, but not limited to, —S(O)— and —S(O)$_2$—. For example, heteroalkyl can include ethers, thioethers, alkyl-amines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

The term "heterocycloalkyl" refers to a ring system having from 3 ring members to about 20 ring members and from 1 to about 5 heteroatoms such as N, O and S. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

The term "heterocycloalkylene" refers to a heterocyclalkyl group, as defined above, linking at least two other groups. The two moieties linked to the heterocycloalkylene can be linked to the same atom or different atoms of the heterocycloalkylene.

The term "optionally substituted" is used herein to indicate a moiety that can be unsubstituted or substituted by one or more substituent. When a moiety term is used without specifically indicating as substituted, the moiety is unsubstituted.

To overcome the current obstacles associated with developing high-energy full-cells with Si-based anodes, the next generation of oxidation-stable electrolytes or electrolyte additives are developed. The electrolyte or electrolyte additives can form a stable, electronically insulating but ionically conducting SEI layer on the surface of Si anodes. Additionally, these electrolytes or additives may also help modify cathode surfaces, forming stable CEI layers. These could enable the electrochemical stability of Li-ion batteries when cycled at higher voltages and help with calendar life of the batteries. In addition, to alleviate battery safety concerns, these additives may impart an increased thermal stability to the organic components of the electrolyte, drive a rise in the flash point of the electrolyte formulations, increase the flame-retardant effectiveness and enhance thermal stability of SEI or CEI layers on the surface of electrodes. Further, the additives may produce one or more of the following benefits: increased energy density, increased safety, decreased electrolyte consumption and/or decreased gassing.

In the present disclosure, the use of chemical compounds comprising symmetrical or asymmetrical alkylsulfonyl imide or cyclic alkylene sulfonylimide salts as electrode or electrolyte additives for energy storage devices is described. Due to their unique chemical structures and functional groups, using symmetrical or asymmetrical alkylsulfonyl imide or cyclic alkylene sulfonylimide salts as electrolyte additives in electrolyte compositions may bring the following benefits: (i) stabilize solid/electrolyte interface film to reduce electrolyte reactions (oxidation on the NCM, NCA, or LCO cathode and reduction on the Si anode), prevent Si anode volume expansion, and protect transition metal ion dissolution from NCM or NCA cathodes and stabilize the subsequent structure changes; and avoid the exothermic reaction between the released oxygen from cathodes and an organic electrolyte and enhance the thermal stability of cathodes; and (ii) reduce the flammability and enhance the thermal stability of organic electrolytes and increase the safety of electrolyte solutions. Due to their versatility in reaction chemistry and overall stability in electrochemical environments, involving symmetrical or asymmetrical alkylsulfonyl imide or cyclic alkylene sulfonylimide salts as electrolyte additives in electrolyte compositions may help improve both overall electrochemical performance and safety of Si anode-based Li-ion batteries. In some embodiments, the additive is a perfluoroalkylsulfonyl imide or acyclic perfluoroalkylene sulfonylimide salt.

Typical carbon anode electrodes include a current collector such as a copper sheet. Carbon is deposited onto the collector along with an inactive binder material. Carbon is often used because it has excellent electrochemical properties and is also electrically conductive. If the current collector layer (e.g., copper layer) was removed, the carbon would likely be unable to mechanically support itself. Therefore, conventional electrodes require a support structure such as the collector to be able to function as an electrode. The electrode (e.g., anode or cathode) compositions described in this application can produce electrodes that are self-supported. The need for a metal foil current collector is eliminated or minimized because conductive carbonized polymer is used for current collection in the anode structure as well as for mechanical support. In typical applications for the mobile industry, a metal current collector is typically added to ensure sufficient rate performance. The carbonized polymer can form a substantially continuous conductive carbon phase in the entire electrode as opposed to particulate carbon suspended in a non-conductive binder in one class of conventional lithium-ion battery electrodes. Advantages of a carbon composite blend that utilizes a carbonized polymer can include, for example, 1) higher capacity, 2) enhanced overcharge/discharge protection, 3) lower irreversible capacity due to the elimination (or minimization) of metal foil current collectors, and 4) potential cost savings due to simpler manufacturing.

Anode electrodes (negative electrodes) currently used in the rechargeable lithium-ion cells typically have a specific capacity of approximately 200 milliamp hours per gram (including the metal foil current collector, conductive additives, and binder material). Graphite, the active material used in most lithium ion battery anodes, has a theoretical energy density of 372 milliamp hours per gram (mAh/g). In comparison, silicon has a high theoretical capacity of up to 4200 mAh/g. In order to increase volumetric and gravimetric energy density of lithium-ion batteries, silicon may be used as the active material for the cathode or anode. Several types of silicon materials, e.g., silicon nanopowders, silicon nanofibers, porous silicon, and ball-milled silicon, have also been reported as viable candidates as active materials for the negative or positive electrodes. Small particle sizes (for example, sizes in the nanometer range) generally can increase cycle life performance. They also can display very high initial irreversible capacity. However, small particle sizes also can result in very low volumetric energy density (for example, for the overall cell stack) due to the difficulty of packing the active material. Larger particle sizes, (for example, sizes in the micron range) generally can result in higher density anode material. However, the expansion of the silicon active material can result in poor cycle life due to particle cracking. For example, silicon can swell in excess of 300% upon lithium insertion. Because of this expansion, anodes including silicon should be allowed to expand while maintaining electrical contact between the silicon particles.

Cathode electrodes (positive electrodes) described herein may include metal oxide cathode materials, such as Lithium Cobalt Oxide ($LiCoO_2$) (LCO), Ni-rich oxides, high voltage cathode materials, lithium-rich oxides, nickel-rich layered oxides, lithium rich layered oxides, high-voltage spinel oxides, and high-voltage polyanionic compounds. Ni-rich oxides and/or high voltage cathode materials may include NCM and NCA. One example of a NCM material includes $LiNi_{0.6}Co_{0.2}Mn_{0.2}O_2$ (NCM-622). Lithium rich oxides may include $xLi_2Mn_3O_2 \cdot (1-x)LiNi_aCo_bMn_cO_2$. Nickel-rich layered oxides may include $LiNi_{1+x}M_{1-x}O_z$ (where M=Co, Mn or Al). Lithium rich layered oxides may include $LiNi_{1+x}M_{1-x}O_2$ (where M=Co, Mn or Ni). High-voltage spinel oxides may include $LiNi_{0.5}Mn_{1.5}O_4$. High-voltage polyanionic compounds may include phosphates, sulfates, silicates, etc. I In certain embodiments, the positive electrode may be one of NCA, NCM, LMO or LCO. The NCM cathodes include NCM 9 0.5 0.5, NCM811, NCM622, NCM532, NCM433, NCM111, and others. In further embodiments, the positive electrode comprises a lithium-rich layered oxide $xLi_2MnO_3 \cdot (1-x)LiNi_aCo_bMn_cO_2$; nickel-rich layered oxide $LiNi_{1-x}M_xO_2$ (M=Co, Mn and Al); or lithium rich layered oxide $LiNi_{1+x}M_{1-x}O_2$ (M=Co, Mn and Ni) cathode.

In the present disclosure, the use of chemical compounds comprising symmetrical or asymmetrical alkylsulfonyl imide or cyclic alkylene sulfonylimide metal salts as electrode additives for Si anode-based Li-ion batteries (including directly coated Si-dominant anodes with or without further thermal treatments, laminated Si-dominant anodes, and all other Si anodes) with different cathodes is described. Symmetrical or asymmetrical alkylsulfonyl imide or cyclic oalkylene sulfonylimide metal salts may be added directly to electrode slurries, such as a cathode slurry to prepare additive-containing cathodes including, but not limited to, those listed above. In some embodiments, the symmetrical or asymmetrical alkylsulfonyl imide or cyclic alkylene sulfonylimide lithium salts may be used as Si anode additives by directly adding them into the Si anode slurry to prepare additive-containing direct-coated Si-dominant anodes (with or without further thermal treatment at high temperature) or laminated Si-dominant anodes after pyrolysis. The Si anodes may be Si-dominant anodes, directly coated Si-dominant anodes, or coated Si anodes with polymer binder and carbon black. Additionally described is the use of symmetrical or asymmetrical alkylsulfonyl imide or cyclic alkylene sulfonylimide metal salts as cathode additives for different types of cathode-based Li-ion full cells or as electrolyte additives in electrolyte compositions. In some embodiments, symmetrical or asymmetrical alkylsulfonyl imide or cyclic alkylene sulfonylimide lithium salts may be used as electrolyte additives to improve the performance of Si anode-based Li-ion full cells with different cathodes. In some embodiments, the additive is a perfluoroalkylsulfonyl imide or acyclic perfluoroalkylene sulfonylimide salt.

As described herein and in U.S. patent application Ser. Nos. 13/008,800 and 13/601,976, entitled "Composite Materials for Electrochemical Storage" and "Silicon Particles for Battery Electrodes," respectively, certain embodiments utilize a method of creating monolithic, self-supported anodes using a carbonized polymer. Because the polymer is converted into an electrically conductive and electrochemically active matrix, the resulting electrode is conductive enough that, in some embodiments, a metal foil or mesh current collector can be omitted or minimized. The converted polymer also acts as an expansion buffer for silicon particles during cycling so that a high cycle life can be achieved. In certain embodiments, the resulting electrode is an electrode that is comprised substantially of active material. In further embodiments, the resulting electrode is substantially active material. The electrodes can have a high energy density of between about 500 mAh/g to about 1200 mAh/g that can be due to, for example, 1) the use of silicon, 2) elimination or substantial reduction of metal current collectors, and 3) being comprised entirely or substantially entirely of active material.

As described herein and in U.S. patent application Ser. No. 14/800,380, entitled "Electrolyte Compositions for Batteries," the entirety of which is hereby incorporated by reference, composite materials can be used as an anode in most conventional Li-ion batteries; they may also be used as the cathode in some electrochemical couples with additional additives. The composite materials can also be used in either secondary batteries (e.g., rechargeable) or primary batteries (e.g., non-rechargeable). In some embodiments, the composite materials can be used in batteries implemented as a pouch cell, as described in further details herein. In certain embodiments, the composite materials are self-supported structures. In further embodiments, the composite materials are self-supported monolithic structures. For example, a collector may be included in the electrode comprised of the composite material. In certain embodiments, the composite material can be used to form carbon structures discussed in U.S. patent application Ser. No. 12/838,368 entitled "Carbon Electrode Structures for Batteries," the entirety of which is hereby incorporated by reference. Furthermore, the composite materials described herein can be, for example, silicon composite materials, carbon composite materials, and/or silicon-carbon composite materials.

In some embodiments, a largest dimension of the silicon particles can be less than about 40 μm, less than about 1 μm, between about 10 nm and about 40 μm, between about 10 nm and about 1 μm, less than about 500 nm, less than about 100 nm, and about 100 nm. All, substantially all, or at least some of the silicon particles may comprise the largest dimension described above. For example, an average or median largest dimension of the silicon particles can be less than about 40 μm, less than about 1 μm, between about 10 nm and about 40 μm, between about 10 nm and about 1 μm, less than about 500 nm, less than about 100 nm, and about 100 nm. The amount of silicon in the composite material can be greater than zero percent by weight of the mixture and composite material. In certain embodiments, the mixture comprises an amount of silicon, the amount being within a range of from about 0% to about 95% by weight, including from about 30% to about 95% by weight of the mixture. The amount of silicon in the composite material can be within a range of from about 0% to about 35% by weight, including from about 0% to about 25% by weight, from about 10% to about 35% by weight, and about 20% by weight. In further certain embodiments, the amount of silicon in the mixture is at least about 30% by weight. Additional embodiments of the amount of silicon in the composite material include more than about 50% by weight, between about 30% and about 95% by weight, between about 50% and about 85% by weight, and between about 75% and about 95% by weight. Furthermore, the silicon particles may or may not be pure silicon. For example, the silicon particles may be substantially silicon or may be a silicon alloy. In one embodiment, the silicon alloy includes silicon as the primary constituent along with one or more other elements.

As described herein, micron-sized silicon particles can provide good volumetric and gravimetric energy density combined with good cycle life. In certain embodiments, to obtain the benefits of both micron-sized silicon particles (e.g., high energy density) and nanometer-sized silicon particles (e.g., good cycle behavior), silicon particles can have an average particle size in the micron range and a surface including nanometer-sized features. In some embodiments, the silicon particles have an average particle size (e.g., average diameter or average largest dimension) between about 0.1 μm and about 30 μm or between about 0.1 μm and all values up to about 30 μm. For example, the silicon particles can have an average particle size between about 0.5 μm and about 25 μm, between about 0.5 μm and about 20 μm, between about 0.5 μm and about 15 μm, between about 0.5 μm and about 10 μm, between about 0.5 μm and about 5 μm, between about 0.5 μm and about 2 μm, between about 1 μm and about 20 μm, between about 1 μm and about 15 μm, between about 1 μm and about 10 μm, between about 5 μm and about 20 μm, etc. Thus, the average particle size can be any value between about 0.1 μm and about 30 μm, e.g., 0.1 μm, 0.5 μm, 1 μm, 5 μm, 10 μm, 15 μm, 20 μm, 25 μm, and 30 μm.

The composite material can be formed by pyrolyzing a polymer precursor, such as polyamide acid. The amount of carbon obtained from the precursor can be about 50 weight percent by weight of the composite material. In certain embodiments, the amount of carbon from the precursor in the composite material is about 10% to about 25% by weight. The carbon from the precursor can be hard carbon. Hard carbon can be a carbon that does not convert into graphite even with heating in excess of 2800 degrees Celsius. Precursors that melt or flow during pyrolysis convert into soft carbons and/or graphite with sufficient temperature and/or pressure. Hard carbon may be selected since soft carbon precursors may flow and soft carbons and graphite are mechanically weaker than hard carbons. Other possible hard carbon precursors can include phenolic resins, epoxy resins, and other polymers that have a very high melting point or are crosslinked. A soft carbon precursor can be used if it does not melt at the heat treatment temperatures used. In some embodiments, the amount of carbon in the composite material has a value within a range of from about 10% to about 25% by weight, about 20% by weight, or more than about 50% by weight. In certain embodiments, the carbon phase is substantially amorphous. In other embodiments, the carbon phase is substantially crystalline. In further embodiments, the carbon phase includes amorphous and crystalline carbon. The carbon phase can be a matrix phase in the composite material. The carbon can also be embedded in the pores of the additives including silicon. The carbon may react with some of the additives to create some materials at interfaces. For example, there may be a silicon carbide layer between silicon particles and the carbon.

In certain embodiments, graphite particles are added to the mixture. Advantageously, graphite can be an electrochemically active material in the battery as well as an elastic deformable material that can respond to volume change of the silicon particles. Graphite is the preferred active anode material for certain classes of lithium-ion batteries currently on the market because it has a low irreversible capacity. Additionally, graphite is softer than hard carbon and can better absorb the volume expansion of silicon additives. In certain embodiments, a largest dimension of the graphite particles is between about 0.5 microns and about 20 microns. All, substantially all, or at least some of the graphite particles may comprise the largest dimension described herein. In further embodiments, an average or median largest dimension of the graphite particles is between about 0.5 microns and about 20 microns. In certain embodiments, the mixture includes greater than 0% and less than about 80% by weight of graphite particles. In further embodiments, the composite material includes about 1% to about 20% by weight graphite particles. In further embodiments, the composite material includes about 40% to about 75% by weight graphite particles.

In certain embodiments, conductive particles which may also be electrochemically active are added to the mixture. Such particles can enable both a more electronically conductive composite as well as a more mechanically deformable composite capable of absorbing the large volumetric change incurred during lithiation and de-lithiation. In certain embodiments, a largest dimension of the conductive particles is between about 10 nanometers and about 7 millimeters. All, substantially all, or at least some of the conductive particles may comprise the largest dimension described herein. In further embodiments, an average or median largest dimension of the conductive particles is between about 10 nm and about 7 millimeters. In certain embodiments, the mixture includes greater than zero and up to about 80% by weight conductive particles. In further embodiments, the composite material includes about 45% to about 80% by weight conductive particles. The conductive particles can be conductive carbon including carbon blacks, carbon fibers, carbon nanofibers, carbon nanotubes, graphite, graphene, etc. Many carbons that are considered as conductive additives that are not electrochemically active become active once pyrolyzed in a polymer matrix. Alternatively, the conductive particles can be metals or alloys including copper, nickel, or stainless steel.

The composite material may also be formed into a powder. For example, the composite material can be ground into a powder. The composite material powder can be used as an active material for an electrode. For example, the composite material powder can be deposited on a collector in a manner similar to making a conventional electrode structure, as known in the industry.

In some embodiments, the full capacity of the composite material may not be utilized during use of the battery to improve battery life (e.g., number charge and discharge cycles before the battery fails or the performance of the battery decreases below a usability level). For example, a composite material with about 70% by weight silicon particles, about 20% by weight carbon from a precursor, and about 10% by weight graphite may have a maximum gravimetric capacity of about 2000 mAh/g, while the composite material may only be used up to a gravimetric capacity of about 550 to about 850 mAh/g. Although, the maximum gravimetric capacity of the composite material may not be utilized, using the composite material at a lower capacity can still achieve a higher capacity than certain lithium ion batteries. In certain embodiments, the composite material is used or only used at a gravimetric capacity below about 70% of the composite material's maximum gravimetric capacity. For example, the composite material is not used at a gravimetric capacity above about 70% of the composite material's maximum gravimetric capacity. In further embodiments, the composite material is used or only used at a gravimetric capacity below about 60% of the composite material's maximum gravimetric capacity or below about 50% of the composite material's maximum gravimetric capacity.

An electrolyte composition for a lithium ion battery can include a solvent and a lithium ion source, such as a lithium-containing salt. The composition of the electrolyte may be selected to provide a lithium ion battery with improved performance. In some embodiments, the electrolyte may contain an electrolyte additive. As described herein, a lithium ion battery may include a first electrode, a second electrode, a separator between the first electrode and the second electrode, and an electrolyte in contact with the first electrode, the second electrode, and the separator. The electrolyte serves to facilitate ionic transport between the first electrode and the second electrode. In some embodiments, the first electrode and the second electrode can refer to anode and cathode or cathode and anode, respectively.

In lithium-ion batteries, the most widely used electrolytes are non-aqueous liquid electrolytes; these may comprise a lithium-containing salt (e.g. LiPF6) and low molecular weight carbonate solvents as well as various small amounts of functional additives. LiPF6 holds a dominant position in commercial liquid electrolytes due to its well-balanced properties. However, LiPF6 has problems such as high reactivity towards moisture and poor thermal stability. These issues are primarily attributed to the equilibrium decomposition reaction of LiPF6. The P—F bond in LiPF6 and PF5 is rather labile towards hydrolysis by inevitable trace amounts of moisture in batteries. Besides, as a strong Lewis acid, PF5 is also able to initiate reactions with carbonate solvents, and causes further electrolyte degradation. Moreover, a rise in temperature further accelerates the decomposition reaction of LiPF6 and consequently promotes subsequent parasitic reactions. This is also a reason for faster aging of current lithium-ion batteries at elevated temperatures, as compared to room temperature.

In some embodiments, the electrolyte for a lithium ion battery may include o solvent comprising a fluorine-containing component, such as a fluorine-containing cyclic carbonate, a fluorine-containing linear carbonate, and/or a fluoroether. In some embodiments, the electrolyte can include more than one solvent. For example, the electrolyte may include two or more co-solvents. In some embodiments, at least one of the co-solvents in the electrolyte is a fluorine-containing compound. In some embodiments, the fluorine-containing compound may be fluoroethylene carbonate (FEC), or difluoroethylene carbonate (F2EC). In some embodiments, the co-solvent may be selected from the group consisting of FEC, ethyl methyl carbonate (EMC), 1,1,2,2-tetrafluoroethyl 2,2,3,3-tetrafluoropropyl ether, difluoroethylene carbonate (F2EC), ethylene carbonate (EC), diethyl carbonate (DEC), dimethyl carbonate (DMC), propylene carbonate (PC), Dimethoxy ethane (DME), and gamma-butyrolactone (GBL), methyl acetate (MA), ethyl acetate (EA), and methyl propanoate. In some embodiments, the electrolyte contains FEC. In some embodiments, the electrolyte contains both EMC and FEC. In some embodiments, the electrolyte may further contain 1,1,2,2-tetrafluoroethyl 2,2,3,3-tetrafluoropropyl ether, EC, DEC, DMC, PC, GBL, and/or F2EC or some partially or fully fluorinated linear or cyclic carbonates, ethers, etc. as a co-solvent. In some embodiments, the electrolyte is free or substantially free of non-fluorine-containing cyclic carbonates, such as EC, GBL, and PC.

In further embodiments, electrolyte solvents may be composed of a cyclic carbonate, such as fluoro ethylene carbonate (FEC), di-fluoroethylene carbonate (DiFEC), Trifluoropropylene carbonate (TFPC), ethylene carbonate (EC), propylene carbonate (PC), etc; a linear carbonate, such as dimethyl carbonate (DMC), diethyl carbonate (DEC), ethyl methyl carbonate (EMC), etc, or other solvents, such as methyl acetate, ethyl acetate, or gamma butyrolactone, dimethoxyethane, 1,1,2,2-tetrafluoroethyl 2,2,3,3-tetrafluoropropyl ether, etc.

In some embodiments, the electrolyte composition may comprise a system of solvents (i.e. a solvent, plus one or more co-solvents). The solvents may be fluorinated or non-fluorinated. In some embodiments, the co-solvents may be one or more linear carbonates, lactones, acetates, propanoates and/or non-linear carbonates. In some embodiments, the co-solvents may be one or more carbonate solvents, such as one or more linear carbonates and/or non-linear carbonates, as discussed above. In some embodiments, an electrolyte composition may comprise one or more of EC at a concentration of 5% or more; FEC at a concentration of 5% or more; and/or TFPC at a concentration of 5% or more.

In some embodiments, the solvents in the electrolyte composition include, but are not limited to, one or more of ethyl methyl carbonate (EMC), methyl acetate, dimethyl carbonate (DMC), diethyl carbonate (DEC), gamma butyrolactone, methyl acetate (MA), ethyl acetate (EA), methyl propanoate, fluoro ethylene carbonate (FEC), di-fluoroethylene carbonate (DiFEC), Trifluoropropylene carbonate (TFPC), ethylene carbonate (EC), vinylene carbonate (VC) or propylene carbonate (PC). In further embodiments, the solvents include at least one of one or more of ethyl methyl carbonate (EMC), methyl acetate, dimethyl carbonate (DMC), diethyl carbonate (DEC), gamma butyrolactone, methyl acetate (MA), ethyl acetate (EA), methyl propanoate, along with at least one or more of fluoro ethylene carbonate (FEC), di-fluoroethylene carbonate (DiFEC), Trifluoropropylene carbonate (TFPC), ethylene carbonate (EC), vinylene carbonate (VC) or propylene carbonate (PC).

As used herein, a co-solvent of an electrolyte has a concentration of at least about 10% by volume (vol %). In some embodiments, a co-solvent of the electrolyte may be about 20 vol %, about 40 vol %, about 60 vol %, or about 80 vol %, or about 90 vol % of the electrolyte. In some embodiments, a co-solvent may have a concentration from about 10 vol % to about 90 vol %, from about 10 vol % to about 80 vol %, from about 10 vol % to about 60 vol %, from about 20 vol % to about 60 vol %, from about 20 vol % to about 50 vol %, from about 30 vol % to about 60 vol %, or from about 30 vol % to about 50 vol %.

For example, in some embodiments, the electrolyte may contain a fluorine-containing cyclic carbonate, such as FEC, at a concentration of about 10 vol % to about 60 vol %, including from about 20 vol % to about 50 vol %, and from about 20 vol % to about 40 vol %. In some embodiments, the electrolyte may comprise a linear carbonate that does not contain fluorine, such as EMC, at a concentration of about 40 vol % to about 90 vol %, including from about 50 vol % to about 80 vol %, and from about 60 vol % to about 80 vol %. In some embodiments, the electrolyte may comprise 1,1,2,2-tetrafluoroethyl 2,2,3,3-tetrafluoropropyl ether at a concentration of from about 10 vol % to about 30 vol %, including from about 10 vol % to about 20 vol %.

In some embodiments, the electrolyte is substantially free of cyclic carbonates other than fluorine-containing cyclic carbonates (i.e., non-fluorine-containing cyclic carbonates). Examples of non-fluorine-containing carbonates include EC, PC, GBL, and vinylene carbonate (VC).

In some embodiments, the electrolyte may further comprise one or more additives. As used herein, an additive of the electrolyte refers to a component that makes up less than 10% by weight (wt %) of the electrolyte. In some embodiments, the amount of each additive in the electrolyte may be from about 0.2 wt % to about 1 wt %, 0.1 wt % to about 2 wt %, 0.2 wt % to about 9 wt %, from about 0.5 wt % to about 9 wt %, from about 1 wt % to about 9 wt %, from about 1 wt % to about 8 wt %, from about 1 wt % to about 8 wt %, from about 1 wt % to about 7 wt %, from about 1 wt % to about 6 wt %, from about 1 wt % to about 5 wt %, from about 2 wt % to about 5 wt %, or any value in between. In some embodiments, the total amount of the additive(s) may be from from about 1 wt % to about 9 wt %, from about 1 wt % to about 8 wt %, from about 1 wt % to about 7 wt %, from about 2 wt % to about 7 wt %, or any value in between. In other embodiments, the percentages of additives may be expressed in volume percent (vol %).

The electrolyte additive may comprise symmetrical or asymmetrical alkylsulfonyl imide or cyclic alkylene sulfonylimide metal salts, which may be fully or partially fluorinated. In some embodiments, the additive is a perfluoroalkylsulfonyl imide or acyclic perfluoroalkylene sulfonylimide salt. In some embodiments, the electrolyte additive compound may be a functional symmetrical or asymmetrical alkylsulfonyl imide or cyclic alkylene sulfonylimide metal salt derivative, which may be optionally substituted. In some embodiments, the electrolyte may contain the compound as an additive at less than 10 weight %; or at less than 5 weight %. Symmetrical or asymmetrical alkylsulfonyl imide or cyclic alkylene sulfonylimide metal salts may have various counter ions, including, but not limited to alkali metals, Li, Na, K, Mg, Ca, Zn, Al, or Cs.

In accordance with the disclosure, symmetrical or asymmetrical alkylsulfonyl imide or cyclic alkylene sulfonylimide metal salts may be used as both electrode additives (cathode or anode) and/or as electrolyte additives in electrolyte compositions.

Example general structures (Ia and Ib) are shown below for symmetrical or asymmetrical alkylsulfonyl imide or cyclic alkylene sulfonylimide metal salts:

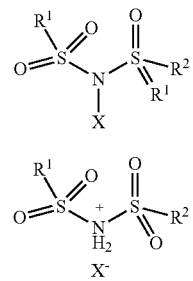

Note that Ia and Ib depict the same structure, where the nitrogen-metal bond is illustrated in two ways—as a covalent bond and as an ionic bond. X may be, for example, an alkali metal: lithium (Li), sodium (Na), potassium (K), rubidium (Rb), cesium (Cs), or francium (Fr) or may be, e.g., Mg, Ca, Zn or Al.

In the above formulas, $R^1$ and $R^2$ may be the same (symmetrical) or different (asymmetrical) and may be selected from the group consisting of H, OH, F, alkyl, fluoro-alkyl, alkylene, alkoxy, alkenyl, alkenylene, alkynyl, alkynylene, cycloalkyl, cycloalkylene, aryl, arylene, heteroaryl, heteroalkyl, heteroalkylene, heterocycloalkyl, and heterocycloalkylene, as defined above, which may be also further optionally substituted. In some embodiments, $R^1$ and $R^2$ may further bond with each other to create a cyclic structure, e.g. cyclic alkylene sulfonylimide metal salts such as Lithium 1,1,2,2,3,3-Hexafluoropropane-1,3-disulfonimide (LHFPDI).

In some embodiments, $R^1$ and $R^2$ may have one or more alkenyl, alkenylene, alkynyl, alkynylene, cycloalkyl, cycloalkylene, aryl, arylene or heteroaryl substituents, which are substituted by H, alkyl, fluoro-alkyl, alkylene, alkoxy, alkenyl, alkenylene, alkynyl, alkynylene, cycloalkyl, cycloalkylene, aryl, arylene, heteroaryl, heteroalkyl, heteroalkylene, heterocycloalkyl, and heterocycloalkylene, as described above, and which may be further optionally substituted.

In some embodiments, the compound may be fluorinated fully e.g., perfluoroalkylsulfonyl imide or acyclic perfluoroalkylene sulfonylimide salts, or partially fluorinated.

In some embodiments, a dimer formed by two sulfonyl imide moieties bound to one ion (e.g., Zinc Di[bis(trifluoromethylsulfonyl)imide]) or a dimer of sulfonamides connected through a moiety such as phenyl, C=O or $SO_2$ (e.g., lithium (1,3-phenylenedisulfonyl) bis(fluoro sulfonyl) imide, lithium carbonylbis(fluorosulfonyl)imide (LiCFSI) or lithium sulfonylbis(fluorosulfonyl)imide (LiSFSI)) is contemplated.

Sulfonyl methanide-type compounds including but not limited to Lithium tris[(trifluoromethyl)sulfonyl]methanide are also contemplated.

In some embodiments, the compound is selected from one or more of Lithium 1,1,2,2,3,3-Hexafluoropropane-1,3-disulfonimide (LHFPDI), Lithium Bis(pentafluoro-ethanesulfonyl)imide (LBPFESF), and Lithium Bis(nonafluorobutanesulfonyl)imide (LBNFBSF), Lithium (fluorosulfonyl) (trifluoromethanesulfonyl)imide, lithium (trifluoromethanesulfonyl) (vinylsulfonyl)imide, Lithium 4-vinyl-N-(trifluoromethane)sulfonylbenzene-1-sulfonamide, lithium bis(1,1,2,2,3,3,3-heptafluoro-1-propanesulfonyl)imide, Lithium (fluorosulfonyl) (nonafluorobutanesulfonyl)imide, lithium (fluorosulfonyl) (pentafluoroethylsulfonyl)imide, lithium (1,3-phenylenedisulfonyl) bis(fluoro sulfonyl) imide, lithium (trifluoromethanesulfonyl) (n-nonafluorobutanesulfonyl)imide (LiTNFSI), lithium; 1,1,2,2,3,3,4,4,4-nonafluoro-N-(1,1,2,2,2-pentafluoroethylsulfonyl)butane-1-sulfonamide, lithium; 1,1,2,2,3,3,4,4,4-nonafluoro-N-(1,1,2,2,3,3,3-heptafluoro-propylsulfonyl)butane-1-sulfonamide, lithium sulfonylbis(fluorosulfonyl)imide (LiSFSI), lithium carbonylbis(fluorosulfonyl)imide (LiCFSI), Lithium-cyclodifluoromethane-1,1-bis(sulfonyl)imide (LiDMSI), lithium 1,2,3-dithiazolidine-4,4,5,5-tetrafluoro-1,1,3,3-tetraoxide, Lithium; 4,4,5,5,6-pentafluoro-6-(trifluoromethyl)-1lambda6,3lambda6-dithia-2-azanidacyclohexane 1,1,3,3-tetraoxide, Lithium tris[(trifluoromethyl) sulfonyl]methanide, Potassium 1,1,2,2,3,3-Hexafluoropropane-1,3-disulfonimide, Potassium bis[(nonafluorobutyl)sulfonyl]azanide, Potassium Bis(nonafluorobutanesulfonyl)imide, Potassium (trifluoromethanesulfonyl) (vinylsulfonyl)imide, Sodium Bis(nonafluorobutanesulfonyl)imide, Calcium(II) Bis(nonafluorobutanesulfonyl)imide, or Zinc Di[bis(trifluoromethylsulfonyl)imide].

Example structures of symmetrical or asymmetrical alkylsulfonyl imide or cyclic alkylene sulfonylimide metal salts are shown below:

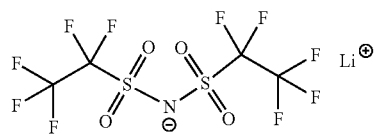 [SMILES: O=S(=O)([N-]S(=O)(=O)C(F)(F)C(F)(F)F)C(F)(F)C(F)(F)F ; [Li+]]

Lithium 1,1,2,2,3,3-Hexafluoropropane-1,3-disulfonimide (LHFPDF)

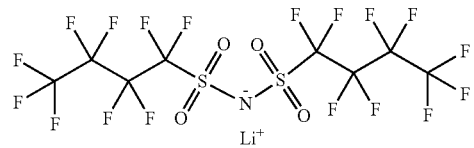 [SMILES: O=S(=O)(NS(=O)(=O)C(F)(F)C(F)(F)C(F)(F)C(F)(F)F)C(F)(F)C(F)(F)C(F)(F)C(F)(F)F ; [Li+]]

Lithium Bis(pentafluoroethanesulfonyl)imide (LBPFESF)

Lithium Bis(nonafluorobutanesulfonyl)imide (LBNFBSF)

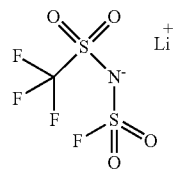

Lithium (fluorosulfonyl)(trifluoromethanesulfonyl)imide

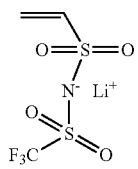

lithium (trifluoromethanesulfonyl)(vinylsulfonyl)imide

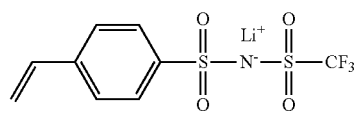

Lithium 4-vinyl-N-(trifluoromethane)sulfonylbenzene-1-sulfonamide

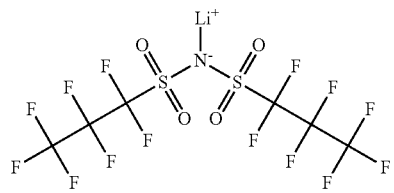

lithium bis(1,1,2,2,3,3,3-heptafluoro-1-propanesulfonyl) imide

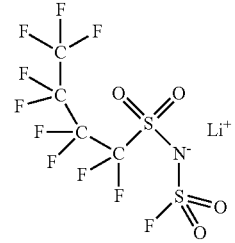 [SMILES: O=S(=O)(F)[N-]S(=O)(=O)C(F)(F)C(F)(F)C(F)(F)C(F)(F)F ; [Li+]]

Lithium (fluorosulfonyl)(nonafluorobutanesulfonyl)imide

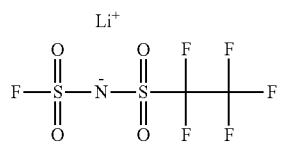

lithium (fluorosulfonyl) (pentafluoroethylsulfonyl)imide

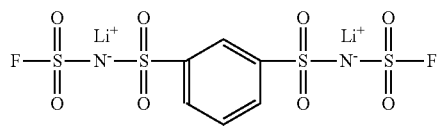

lithium (1,3-phenylenedisulfonyl) bis(fluoro sulfonyl) imide

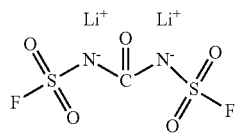

lithium carbonylbis(fluorosulfonyl)imide (LiSFSI)

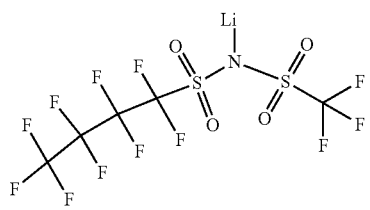

lithium (trifluoromethanesulfonyl) (n-nonafluorobutane-sulfonyl)imide (LiTNFSI)

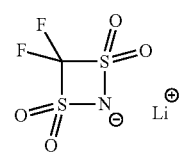

Lithium-cyclo-difluoromethane-1,1-bis(sulfonyl)imide (LiDMSI)

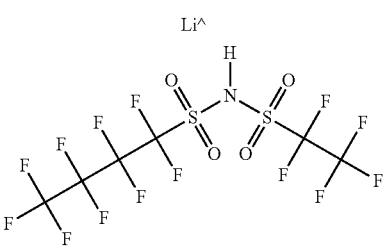 [SMILES: O=S(=O)(NS(=O)(=O)C(F)(F)C(F)(F)C(F)(F)C(F)(F)F)C(F)(F)C(F)(F)F]

lithium; 1,1,2,2,3,3,4,4,4-nonafluoro-N-(1,1,2,2,2-pentafluoroethylsulfonyl)butane-1-sulfonamide

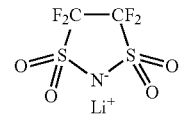

lithium 1,2,3-dithiazolidine-4,4,5,5-tetrafluoro-1,1,3,3-tetraoxide

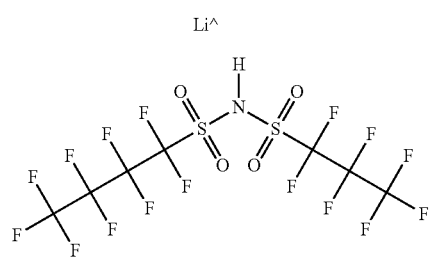 [SMILES: O=S(=O)(NS(=O)(=O)C(F)(F)C(F)(F)C(F)(F)C(F)(F)F)C(F)(F)C(F)(F)C(F)(F)F]

lithium; 1,1,2,2,3,3,4,4,4-nonafluoro-N-(1,1,2,2,3,3,3-heptafluoropropylsulfonyl)butane-1-sulfonamide Lithium; 4,4,5,5,6-pentafluoro-6-(trifluoromethyl)-1lambda6,3lambda6-dithia-2-azanidacyclohexane 1,1,3,3-tetraoxide

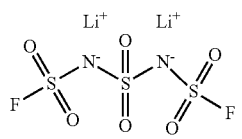

lithium sulfonylbis(fluorosulfonyl)imide (LiSFSI)

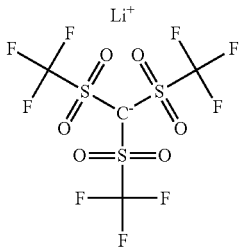 [SMILES: [Li+] ; O=S(=O)([C-](S(=O)(=O)C(F)(F)F)S(=O)(=O)C(F)(F)F)C(F)(F)F]

Lithium tris[(trifluoromethyl)sulfonyl]methanide

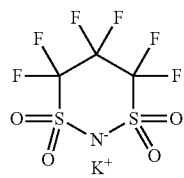 [SMILES: O=S1(=O)[N-]S(=O)(=O)C(F)(F)C(F)(F)C1(F)F ; [K+]]

Potassium 1,1,2,2,3,3-Hexafluoropropane-1,3-disulfonimide

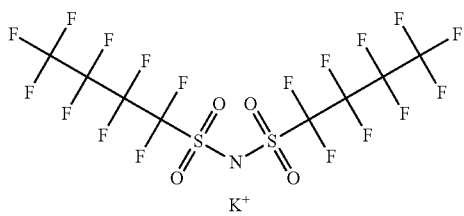 [SMILES: O=S(=O)(NS(=O)(=O)C(F)(F)C(F)(F)C(F)(F)C(F)(F)F)C(F)(F)C(F)(F)C(F)(F)C(F)(F)F ; [K+]]

Potassium bis[(nonafluorobutyl)sulfonyl]azanide

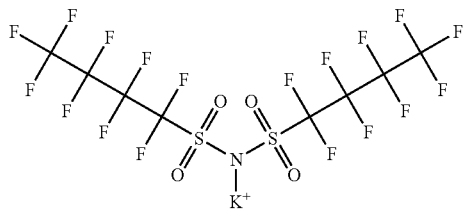

Potassium Bis(nonafluorobutanesulfonyl)imide

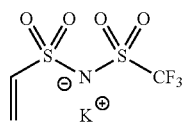

Potassium (trifluoromethanesulfonyl)(vinylsulfonyl)imide

Sodium Bis(nonafluorobutanesulfonyl)imide

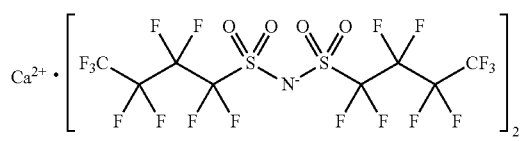

Calcium(II) Bis(nonafluorobutanesulfonyl)imide

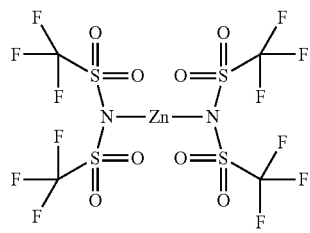

Zinc Di[bis(trifluoromethylsulfonyl)imide]

In some embodiments, any of the symmetrical or asymmetrical alkylsulfonyl imide or cyclic alkylene sulfonylimide metal salt compounds above may be used as electrode additives. In further embodiments, Lithium 1,1,2,2,3,3-Hexafluoropropane-1,3-disulfonimide (LHFPDF), Lithium Bis(pentafluoro-ethanesulfonyl)imide (LBPFESF), or Lithium Bis(nonafluorobutanesulfonyl)imide (LBNFBSF) may be used as electrode additives, including, but not limited to, as Ni-rich NCM or NCA cathode additives for Si-dominant anode-based Li-ion full cells or as electrolyte additives for Si-dominant anode-based Li-ion full cells with different cathodes.

The use of functional compound additives is a viable, economical and cost-effective strategy to modify the surface chemistry in batteries. This allows for potential circumvention of the massive volume change and initial capacity loss due to the continuous electrolyte decomposition in high capacity and reactive electrodes, such as Si anodes, Ni-rich NCA or NCM cathodes. Compound additives can be directly added into the cathode slurries, anode (e.g. Si) slurries or used as electrolyte additives. Additives can modify the SEI or CEI interphases in Li-ion batteries, thus altering and tuning their composition and corresponding electrochemical properties, such as cycle life, rate capability, energy/power densities, etc. In the present disclosure, symmetrical or asymmetrical alkylsulfonyl imide or cyclic alkylene sulfonylimide metal salts are described for use as cathode additives for different types of cathodes, or as electrolyte additives for different Si anode-based Li-ion full cells (which can also be used with the aforementioned cathodes) or as direct anode additives. In some embodiments, the additive is a perfluoroalkylsulfonyl imide or acyclic perfluoroalkylene sulfonylimide salt.

Compound additives, as part of electrolyte and/or electrode compositions, can form a SEI layer that can reduce or prevent the cracking and/or the continuous reduction of electrolyte solutions as the silicon containing anode expands and contracts during cycling. Furthermore, these electrolyte additives, along with the electrolyte solvents, may be oxidized on a cathode surface to form a CEI layer that can suppress or minimize further decomposition of the electrolyte on the surface of the cathode. Without being bound to the theory or mode of operation, it is believed that the presence of symmetrical or asymmetrical alkylsulfonyl imide or cyclic alkylene sulfonylimide metal salts can result in a SEI and/or CEI layer on the surface of electrodes with improved performance. An SEI layer comprising symmetrical or asymmetrical alkylsulfonyl imide or cyclic alkylene sulfonylimide metal salt may demonstrate improved chemical stability and increased density, for example, compared to SEI layers formed by electrolytes without additives or with traditional additives. As such, the change in thickness and surface reactivity of the interface layer are limited, which may in turn facilitate reduction in capacity fade and/or generation of excessive gaseous byproducts during operation of the lithium ion battery. A CEI layer comprising symmetrical or asymmetrical alkylsulfonyl imide or cyclic alkylene sulfonylimide metal salts may help minimize transition metal ion dissolution and structure changes on cathode side and may provide favorable kinetics resulting in improved cycling stability and rate capability.

In some embodiments, other salts may be included in the electrode or electrolyte compositions. A lithium-containing salt for a lithium ion battery may comprise a fluorinated or non-fluorinated salt. In further embodiments, a lithium-containing salt for a lithium ion battery may comprise one or more of lithium hexafluorophosphate ($LiPF_6$), lithium tetrafluoroborate ($LiBF_4$), lithium hexafluoroarsenate monohydrate ($LiAsF_6$), lithium perchlorate ($LiClO_4$), lithium bis(trifluoromethanesulfonyl)imide (LiTFSI), lithium bis(fluorosulfonyl)imide (LiFSI), lithium bis(oxalato)borate (LiBOB), lithium difluoro(oxalate)borate (LiDFOB), lithium triflate ($LiCF_3SO_3$), lithium tetrafluorooxalato phosphate (LTFOP), lithium difluorophosphate ($LiPO_2F_2$), lithium pentafluoroethyltrifluoroborate (LiFAB), and lithium 2-trifluoromethyl-4,5-dicyanoimidazole (LiTDI), lithium bis(2-fluoromalonato)borate (LiBFMB), lithium 4-pyridyl trimethyl borate (LPTB), lithium 2-fluorophenol trimethyl borate (LFPTB), lithium catechol dimethyl borate (LiCDMB), lithium tetrafluorooxalatophosphate (LiFOP), etc. or combinations thereof. In certain embodiments, a lithium-containing salt for a lithium ion battery may comprise lithium hexafluorophosphate (LiPF6). In some embodiments, the electrolyte can have a salt concentration of about 1 moles/L (M). In other embodiments, the salt concentration can be higher than 1 M; in further embodiments, the salt concentration can be higher than 1.2M.

In some embodiments, a lithium ion battery comprising an electrolyte composition according to one or more embodiments described herein, and an anode having a composite electrode film according to one or more embodiments described herein, may demonstrate reduced gassing and/or swelling at about room temperature (e.g., about 20° C. to about 25° C.) or elevated temperatures (e.g., up to temperatures of about 85° C.), increased cycle life at about room temperature or elevated temperatures, and/or reduced cell growth/electrolyte consumption per cycle, for example compared to lithium ion batteries comprising conventionally available electrolyte compositions in combination with an anode having a composite electrode film according to one or more embodiments described herein. In some embodiments, a lithium ion battery comprising an electrolyte composition according to one or more embodiments described herein and an anode having a composite electrode film according to one or more embodiments described herein may demonstrate reduced gassing and/or swelling across various temperatures at which the battery may be subject to testing, such as temperatures between about −20° C. and about 130° C. (e.g., compared to lithium ion batteries comprising conventionally available electrolyte compositions in combination with an anode having a composite electrode film according to one or more embodiments described herein).

Gaseous byproducts may be undesirably generated during battery operation, for example, due to chemical reactions between the electrolyte and one or more other components of the lithium ion battery, such as one or more components of a battery electrode. Excessive gas generation during operation of the lithium ion battery may adversely affect battery performance and/or result in mechanical and/or electrical failure of the battery. For example, undesired chemical reactions between an electrolyte and one or more components of an anode may result in gas generation at levels which can mechanically (e.g., structural deformation) and/or electrochemically degrade the battery. In some embodiments, the composition of the anode and the composition of the electrolyte can be selected to facilitate desired gas generation.

The electrolytes and electrolyte additives described herein may be advantageously utilized within an energy storage device. In some embodiments, energy storage devices may include batteries, capacitors, and battery-capacitor hybrids. In some embodiments, the energy storage device comprise lithium. In some embodiments, the energy storage device may comprise at least one electrode, such as an anode and/or cathode. In some embodiments, at least one electrode may be a Si-based electrode. In some embodiments, the Si-based electrode is a Si-dominant electrode, where silicon is the majority of the active material used in the electrode (e.g., greater than 50% silicon). In some embodiments, the energy storage device comprises a separator. In some embodiments, the separator is between a first electrode and a second electrode.

In some embodiments, the amount of silicon in the electrode material (active material) includes between about 30% and about 95% by weight, between about 50% and about 85% by weight, and between about 75% and about 95% by weight. In other embodiments, the amount of silicon in the electrode material may be at least about 30% by weight; greater than 0% and less than about 95% by weight; or between about 50% and about 95% by weight. Furthermore, the silicon particles may or may not be pure silicon. For example, the silicon particles may be substantially silicon or may be a silicon alloy. In one embodiment, the silicon alloy includes silicon as the primary constituent along with one or more other elements.

In some embodiments, the energy storage device comprises an electrolyte composition. In some embodiments, the electrolyte composition comprises a solvent, solvent additive and/or additive compound as described herein. For example, in some embodiments, the electrolyte comprises an additive compounds comprising a symmetrical or asymmetrical alkylsulfonyl imide or cyclic alkylene sulfonylimide metal salt as described herein. In some embodiments, the additive is a perfluoroalkylsulfonyl imide or acyclic perfluoroalkylene sulfonylimide salt.

As described herein, a battery can be implemented as a pouch cell. FIG. 1 shows a cross-sectional schematic diagram of an example of a lithium ion battery 300 implemented as a pouch cell, according to some embodiments. The battery 300 comprises an anode 316 in contact with a negative current collector 308, a cathode 304 in contact with a positive current collector 310, a separator 306 disposed between the anode 316 and the cathode 304. In some embodiments, a plurality of anodes 316 and cathode 304 may be arranged into a stacked configuration with a separator 306 separating each anode 316 and cathode 304. Each negative current collector 308 may have one anode 316 attached to each side; each positive current collector 310 may have one cathode 304 attached to each side. The stacks are immersed in an electrolyte 314 and enclosed in a pouch 312. The anode 302 and the cathode 304 may comprise one or more respective electrode films formed thereon. The number of electrodes of the battery 300 may be selected to provide desired device performance.

With further reference to FIG. 1, the separator 306 may comprise a single continuous or substantially continuous sheet, which can be interleaved between adjacent electrodes of the electrode stack. For example, the separator 306 may be shaped and/or dimensioned such that it can be positioned between adjacent electrodes in the electrode stack to provide desired separation between the adjacent electrodes of the battery 300. The separator 306 may be configured to facilitate electrical insulation between the anode 302 and the cathode 304, while permitting ionic transport between the anode 302 and the cathode 304. In some embodiments, the separator 306 may comprise a porous material, including a porous polyolefin material.

The lithium ion battery 300 may include an electrolyte 314, for example an electrolyte having a composition as described herein. The electrolyte 314 is in contact with the anode 302, the cathode 304, and the separator 306.

With continued reference to FIG. 1, the anode 302, cathode 304 and separator 306 of the lithium ion battery 300 may be enclosed in a housing comprising a pouch 312. In some embodiments, the pouch 312 may comprise a flexible material. For example, the pouch 312 may readily deform upon application of pressure on the pouch 312, including pressure exerted upon the pouch 312 from within the housing. In some embodiments, the pouch 312 may comprise aluminum. For example, the pouch 312 may comprise a laminated aluminum pouch.

In some embodiments, the lithium ion battery 300 may comprise an anode connector (not shown) and a cathode connector (not shown) configured to electrically couple the anodes and the cathodes of the electrode stack to an external circuit, respectively. The anode connector and a cathode connector may be affixed to the pouch 312 to facilitate electrical coupling of the battery 300 to an external circuit. The anode connector and the cathode connector may be affixed to the pouch 312 along one edge of the pouch 312. The anode connector and the cathode connector can be electrically insulated from one another, and from the pouch 312. For example, at least a portion of each of the anode connector and the cathode connector can be within an electrically insulating sleeve such that the connectors can be electrically insulated from one another and from the pouch 312.

Figure 2:
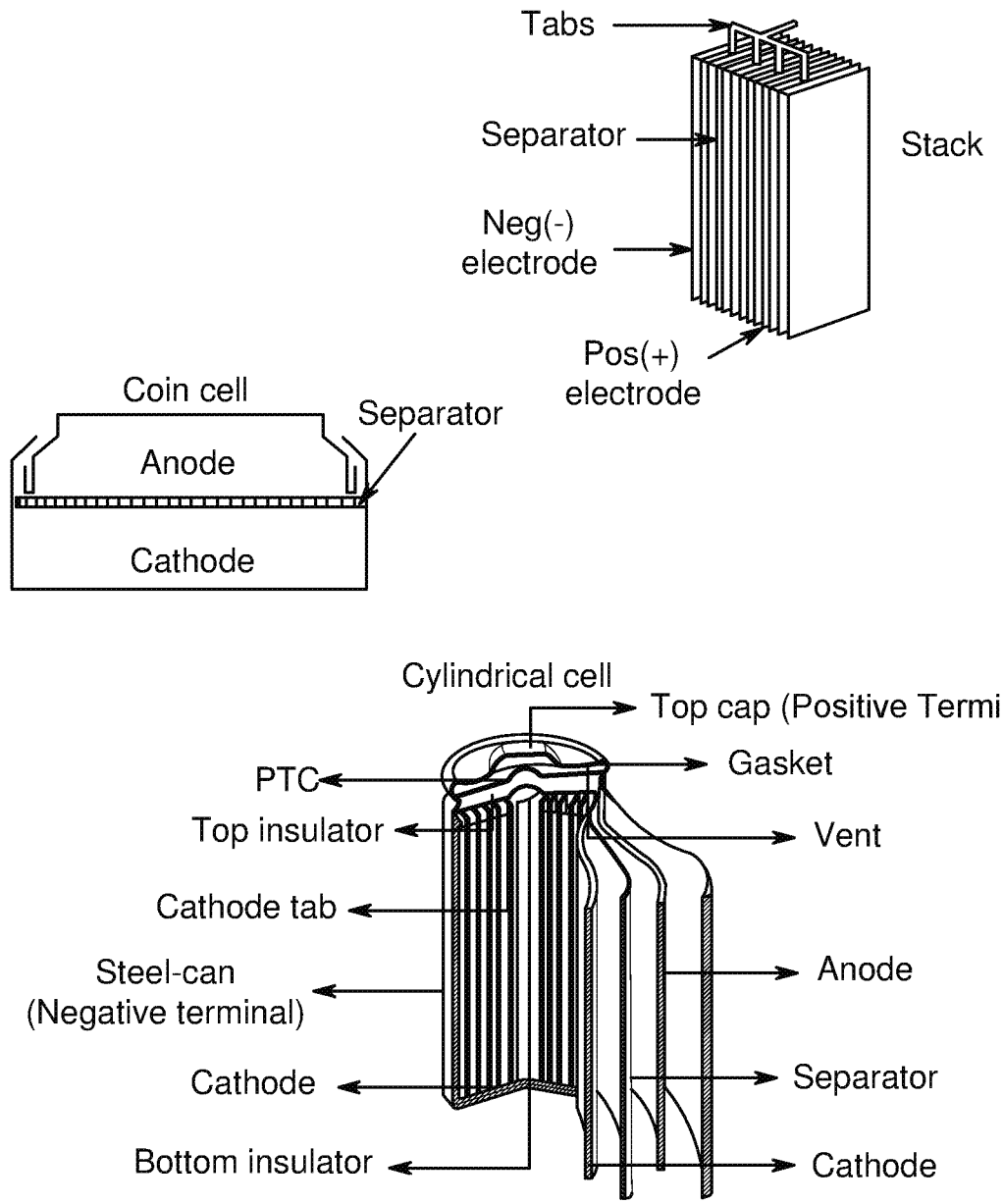
FIG. 2 shows exemplary realistic battery structures, in accordance with an example embodiment of the disclosure.

The cell shown in FIG. 1 is a simplified example to show the principle of operation of a lithium ion cell. Examples of realistic structures are shown in FIG. 2, where stacks of electrodes and separators are utilized, with electrode coatings typically on both sides of the current collectors. The stacks may be formed into different shapes, such as a coin cell, cylindrical cell, or prismatic cell, for example.

Figure 3A:
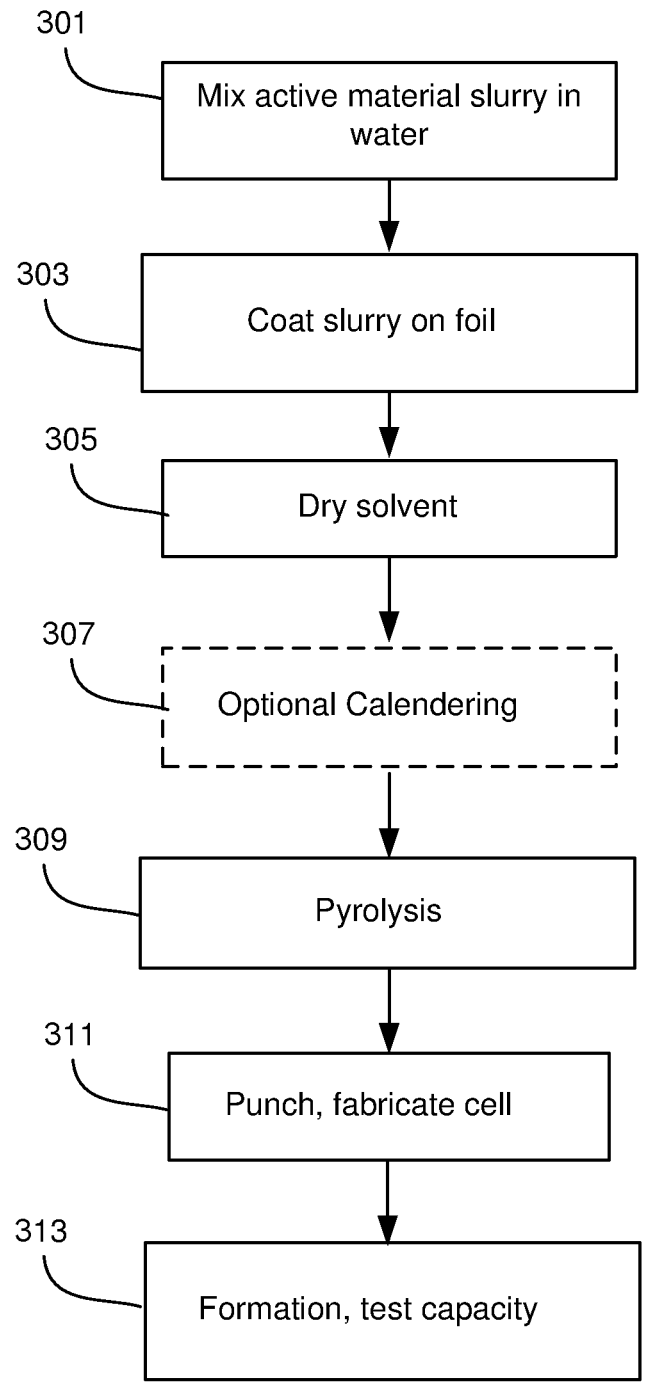
FIGS. 3A and 3B show processes for fabricating cells, in accordance with an example embodiment of the disclosure.

FIG. 3A is a flow diagram of a coating process for fabricating a cell with a silicon-dominant electrode, in accordance with an example embodiment of the disclosure. This process comprises physically mixing the electrode coating layer and conductive additive together, and coating it directly on a current collector as opposed to forming the electrode coating layer on a substrate and then laminating it on a current collector. This strategy may also be adopted by other anode-based cells, such as graphite, conversion type anodes, such as transition metal oxides, transition metal phosphides, and other alloy type anodes, such as Sn, Sb, Al, P, etc.

In step 301, the raw electrode coating layer may be mixed in a slurry comprising electrode materials and an electrolyte composition, which may contain an electrolyte additive.

The particle size (nano to micro) and mixing times may be varied to configure the electrode coating layer density and/or roughness. Furthermore, cathode electrode coating layers may be mixed in step 301, where the electrode coating layer may comprise lithium cobalt oxide (LCO), lithium iron phosphate, lithium nickel cobalt manganese oxide (NMC), Ni-rich lithium nickel cobalt aluminum oxide (NCA), lithium manganese oxide (LMO), lithium nickel manganese spinel, LFP, Li-rich layer cathodes, LNMO or similar materials or combinations thereof, mixed with carbon precursor and additive as described above for the anode electrode coating layer.

In step 303, the as-prepared slurry may be coated on a copper foil, 20 µm thick in this example, and in step 305 may be dried at 130° C. in a convection oven to dry the coating and form the green anode. Similarly, cathode electrode coating layers may be coated on a foil material, such as aluminum, for example.

An optional calendering process may be utilized in step 307 where a series of hard pressure rollers may be used to finish the film/substrate into a smoother and denser sheet of material.

In step 309, the electrode coating layer may be pyrolyzed by heating to 500-800° C., 650° C. in this example, in an inert atmosphere such that carbon precursors are partially or completely converted into conductive carbon. The pyrolysis step may result in an anode electrode coating layer having silicon content greater than or equal to 50% by weight, where the anode has been subjected to heating at or above 400 degrees Celsius.

Pyrolysis can be done either in roll form or after punching in step 311. If done in roll form, the punching is done after the pyrolysis process. In instances where the current collector foil is not pre-punched/pre-perforated, the formed electrode may be perforated with a punching roller, for example. The punched electrodes may then be sandwiched with a separator and electrolyte to form a cell. In step 313, the cell may be subjected to a formation process, comprising initial charge and discharge steps to lithiate the anode, with some residual lithium remaining, and the cell capacity may be assessed. The fabricated anode shows superior adhesion to copper, a remarkable cohesion, and exceptional flexibility. This anode is shown to be capable of fast charging and performs similar or better than current anodes.

Figure 3B:
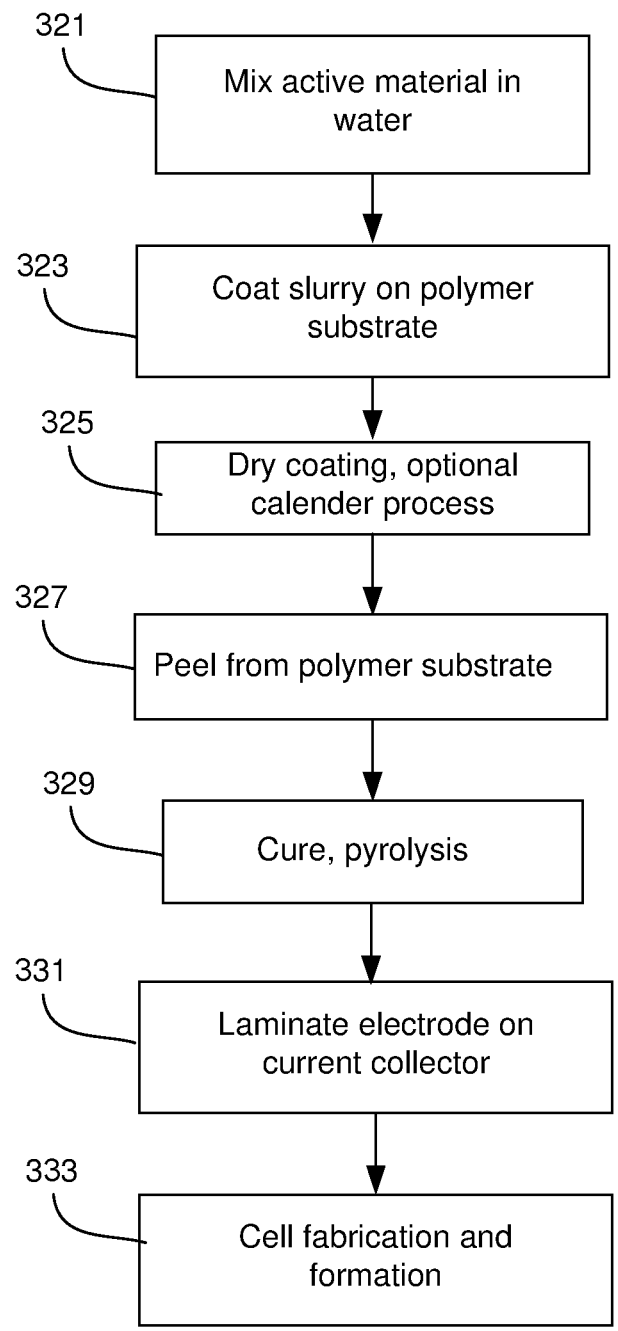

FIG. 3B is a flow diagram of an alternative process for lamination of electrodes, in accordance with an example embodiment of the disclosure. While the previous process to fabricate composite anodes employs a direct coating process, this process physically mixes the active material, conductive additive if desired, and binder together coupled with peeling and lamination processes.

This process is shown in the flow diagram of FIG. 3B, starting with step 321 where the raw electrode coating layer may be mixed in a slurry comprising electrode materials and an electrolyte composition, which may contain an electrolyte additive.

The particle size and mixing times may be varied to configure the electrode coating layer density and/or roughness. Furthermore, cathode electrode coating layers may be mixed in step 321, where the electrode coating layer may comprise lithium cobalt oxide (LCO), lithium iron phosphate, lithium nickel cobalt manganese oxide (NMC), Ni-rich lithium nickel cobalt aluminum oxide (NCA), lithium manganese oxide (LMO), lithium nickel manganese spinel, LFP, Li-rich layer cathodes, LNMO or similar materials or combinations thereof, mixed with carbon precursor and additive as described above for the anode electrode coating layer.

In step 323, the slurry may be coated on a polymer substrate, such as polyethylene terephthalate (PET), polypropylene (PP), or Mylar. The slurry may be coated on the PET/PP/Mylar film at a loading of 3-6 mg/cm2 for the anode and 15-35 mg/cm2 for the cathode, and then dried in step 325. An optional calendering process may be utilized where a series of hard pressure rollers may be used to finish the film/substrate into a smoothed and denser sheet of material.

In step 327, the green film may then be removed from the PET, where the active material may be peeled off the polymer substrate, the peeling process being optional for a polypropylene (PP) substrate, since PP can leave ~2% char residue upon pyrolysis. The peeling may be followed by a cure and pyrolysis step 329 where the film may be cut into sheets, and vacuum dried using a two-stage process (100-140° C. for 14-16 hours, 200-240° C. for 4-6 hours). The dry film may be thermally treated at 1000-1300° C. to convert the polymer matrix into carbon.

In step 331, the pyrolyzed material may be flat press or roll press laminated on the current collector, where for aluminum foil for the cathode and copper foil for the anode may be pre-coated with polyamide-imide with a nominal loading of 0.35-0.75 mg/cm2 (applied as a 5-7 wt % varnish in NMP, dried 10-20 hour at 100-140° C. under vacuum). In flat press lamination, the active material composite film may be laminated to the coated aluminum or copper using a heated hydraulic press (30-70 seconds, 250-350° C., and 3000-5000 psi), thereby forming the finished composite electrode. In another embodiment, the pyrolyzed material may be roll-press laminated to the current collector.

In step 333, the electrodes may then be sandwiched with a separator and electrolyte to form a cell. The cell may be subjected to a formation process, comprising initial charge and discharge steps to lithiate the anode, with some residual lithium remaining, and testing to assess cell performance.

In some aspects, energy storage devices such as batteries are provided. In some embodiments, the energy storage device includes a first electrode and a second electrode, wherein at least one of the first electrode and the second electrode is a Si-based electrode. In some embodiments, the energy storage device includes a separator between the first electrode and the second electrode. In some embodiments, the cathode and/or anode may contain symmetrical or asymmetrical alkylsulfonyl imide or cyclic alkylene sulfonylimide salts as an additive. In further embodiments, the cathode and/or anode may be created using electrode slurries and may contain symmetrical or asymmetrical alkylsulfonyl imide or cyclic alkylene sulfonylimide salts that are added directly to electrode slurries to prepare directly coated electrodes. In some embodiments, the energy storage device includes electrolyte compositions. In some embodiments, the energy storage device includes electrolyte compositions comprising at least one electrolyte additive comprising a symmetrical or asymmetrical alkylsulfonyl imide or cyclic alkylene sulfonylimide salt. Advantages of using symmetrical or asymmetrical alkylsulfonyl imide or cyclic alkylene sulfonylimide salts as electrode or electrolyte additives include, but are not limited to, increased cycle life, increased rate capability and power density and/or decreased impedance increase in electrode interfaces.

In some embodiments, the second electrode is a Si-dominant electrode. In some embodiments, the second electrode comprises a self-supporting composite material film. In some embodiments, the composite material film comprises greater than 0% and less than about 95% by weight of silicon particles, and greater than 0% and less than about 90% by weight of one or more types of carbon phases, wherein at least one of the one or more types of carbon phases is a substantially continuous phase that holds the composite material film together such that the silicon particles are distributed throughout the composite material film.

In some embodiments, the battery may be capable of at least 200 cycles with more than 80% cycle retention when cycling with a C-rate of >2C cycling between an upper voltage of >4V and a lower cut-off voltage of <3.3V. In other embodiments, the battery may be capable of at least 200 cycles with more than 80% cycle retention when cycling with a C-rate of >2C cycling between an upper voltage of >4V and a lower cut-off voltage of <3.3V.

The below example devices and processes for device fabrication are generally described below, and the performances of lithium ion batteries with different electrodes, electrolytes and/or electrolyte additives may be evaluated.

1 wt % Lithium 1,1,2,2,3,3-Hexafluoropropane-1,3-disulfonimide (LHFPDF), 1 wt % Lithium Bis(pentafluoroethanesulfonyl)imide (LBPFESF), and 1 wt % Lithium Bis(nonafluorobutanesulfonyl)imide (LBNFBSF) may be used as NCM811 cathode additives and may be directly added into NCM811 cathode slurries. Three types of these additive-containing NCM811 cathodes may be prepared. After preparation of the cathode, the corresponding Si dominant anode//NCM811 cathode coin full cells may be built and the cells may be tested at 1 C/0.5 C with the voltage window of 4.2V-3.1V.

1 wt % Lithium 1,1,2,2,3,3-Hexafluoropropane-1,3-disulfonimide (LHFPDF), 1 wt % Lithium Bis(pentafluoroethanesulfonyl)imide (LBPFESF), and 1 wt % Lithium Bis(nonafluorobutanesulfonyl)imide (LBNFBSF) may also be used as electrolyte additives by directly adding them into 1.2M LiPF6 in FEC/EMC (3/7 wt %)-based control electrolytes. The corresponding coin full cells may be built with Si-dominant anode//Ni-rich NCM811 or NCA cathodes and the electrochemical performance may be evaluated at 4 C/0.5 C with the voltage window of 4.2V-3.1 V.

Figure 4:
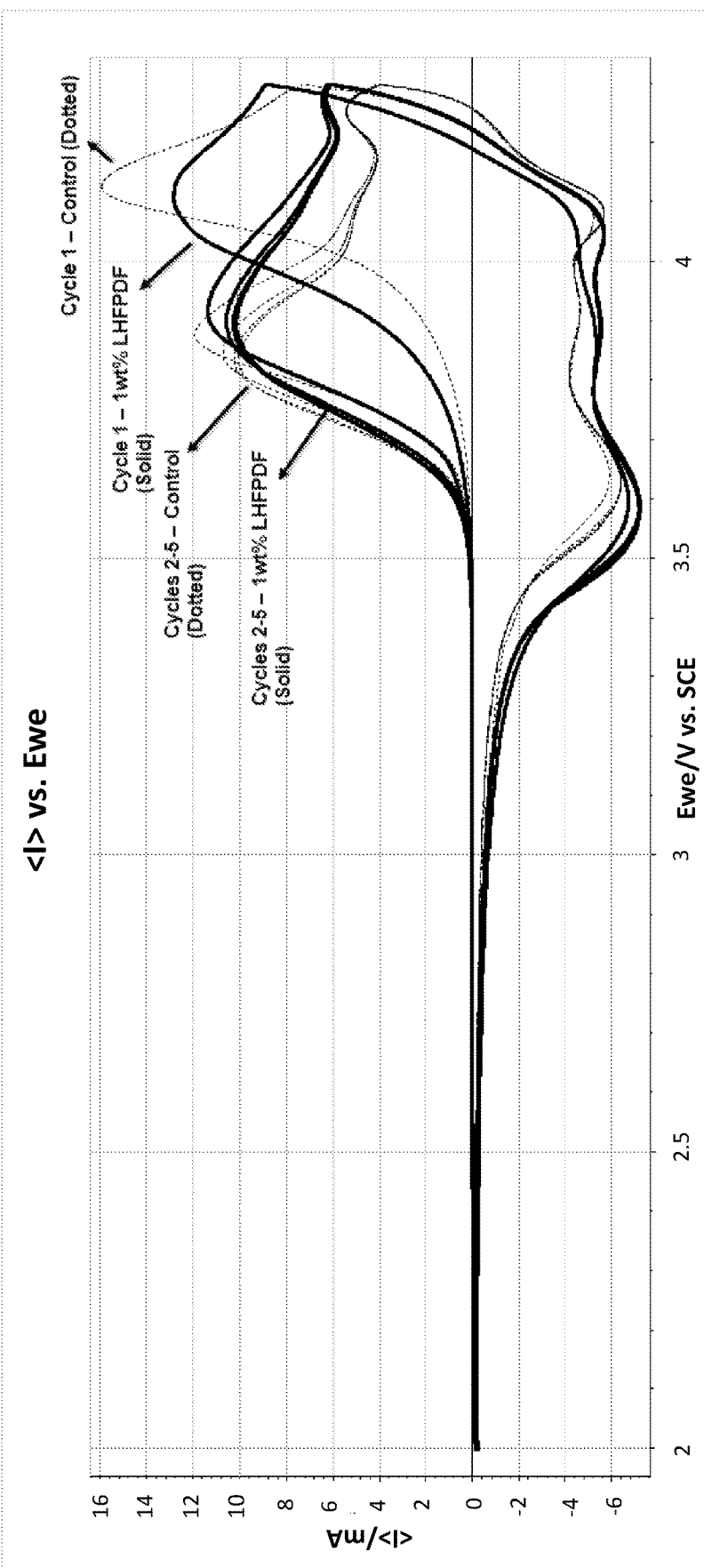
FIG. 4 shows cyclic voltammetry (CV) curves of NCM811 cathode-based coin half cells. The cathodes used may be: (dotted line)—NCM811 Control, (solid line)—1 wt % Lithium 1,1,2,2,3,3-Hexafluoropropane-1,3-disulfonimide (LHFPDF)-containing NCM811, in accordance with an example embodiment of the disclosure.

FIG. 4. Cyclic voltammetry (CV) curves of NCM811 cathode-based coin half cells. The cathodes used may be: (dotted line)—NCM811 Control, (solid line)—1 wt % Lithium 1,1,2,2,3,3-Hexafluoropropane-1,3-disulfonimide (LHFPDF)-containing NCM811. The electrolyte formulation used may be 1.2 M LiPF6 in FEC/EMC (3/7 wt %). The control cathodes contain about 92 wt % NCM811, 4 wt % Super P and 4 wt % PVDF5130, and may be coated on 15 μm Al foil. The average loading may be about 20-30 mg/cm$^2$. The 1 wt % LHFPDF-containing NCM811 cathodes contain about 91 wt % NCM811, 1 wt % LHFPDF, 4 wt % Super P and 4 wt % PVDF5130, and may be coated on 15 μm Al foil with a similar loading with control. The CV measurements may be carried out in the voltage range of 2-4.3 V at a scan rate of 0.2 mV s−1 using VMP3 equipment.

FIG. 4 shows that a clear oxidation peak appears at ~4.15 V (vs. Li/Li+) for the cell with NCM811 cathode (control) in the initial charge. This peak shifts to ~4.10 V (vs. Li/Li$^+$) for the cell of 1 wt % LHFPDF-containing NCM811cathodes in the initial charge. In the following scanning cycles, the oxidation peak related voltage for NCM811 control cathode-based cells shifts to ~3.80 V (vs. Li/Li+); while the cell of 1 wt % LHFPDF-containing NCM811 cathodes becomes wide with the peak center at around 3.75V. In addition, with further scanning, there is an extra shoulder at around 3.85 V.

Figure 5A:
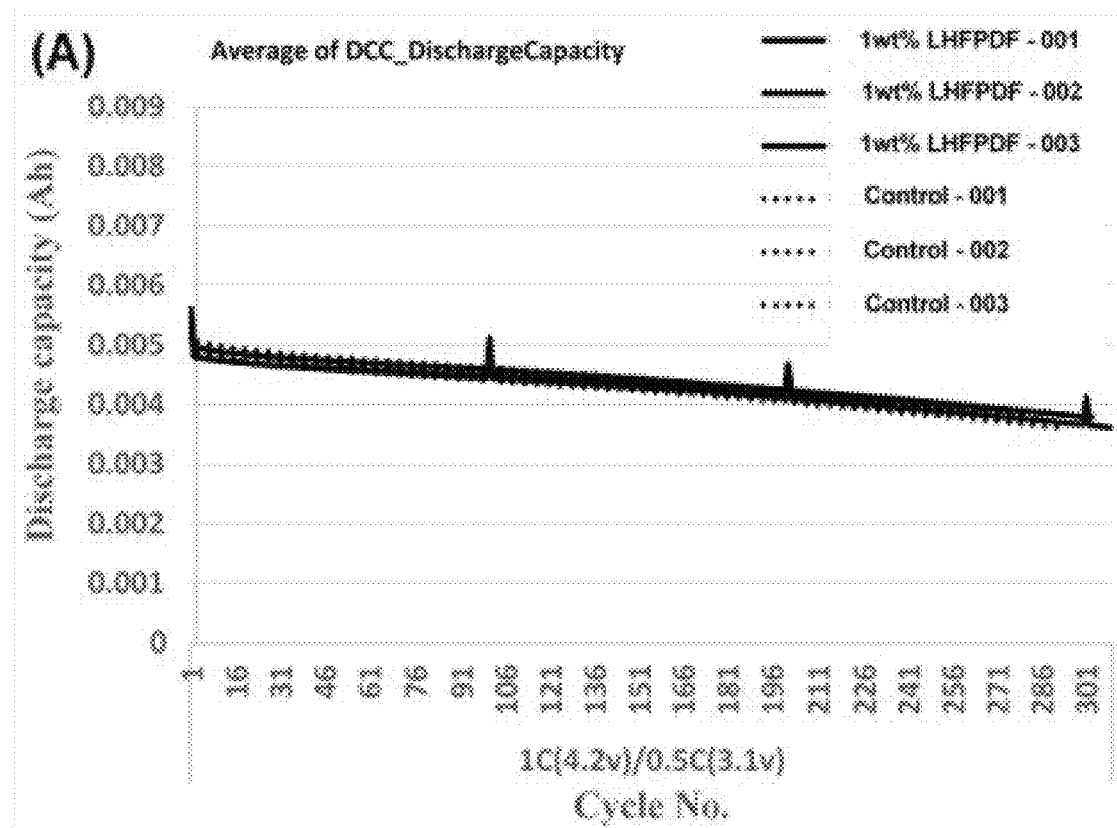
FIGS. 5A and 5B show the capacity retention (FIG. 5A) and normalized capacity retention (FIG. 5B) of Si-dominant anode//NCM811 cathode coin full cells. The cathode used may be: (dotted line)—NCM811 Control, (solid line)—1 wt % Lithium 1,1,2,2,3,3-Hexafluoropropane-1,3-disulfonimide (LHFPDF)-containing NCM811, in accordance with an example embodiment of the disclosure.
Figure 5B:
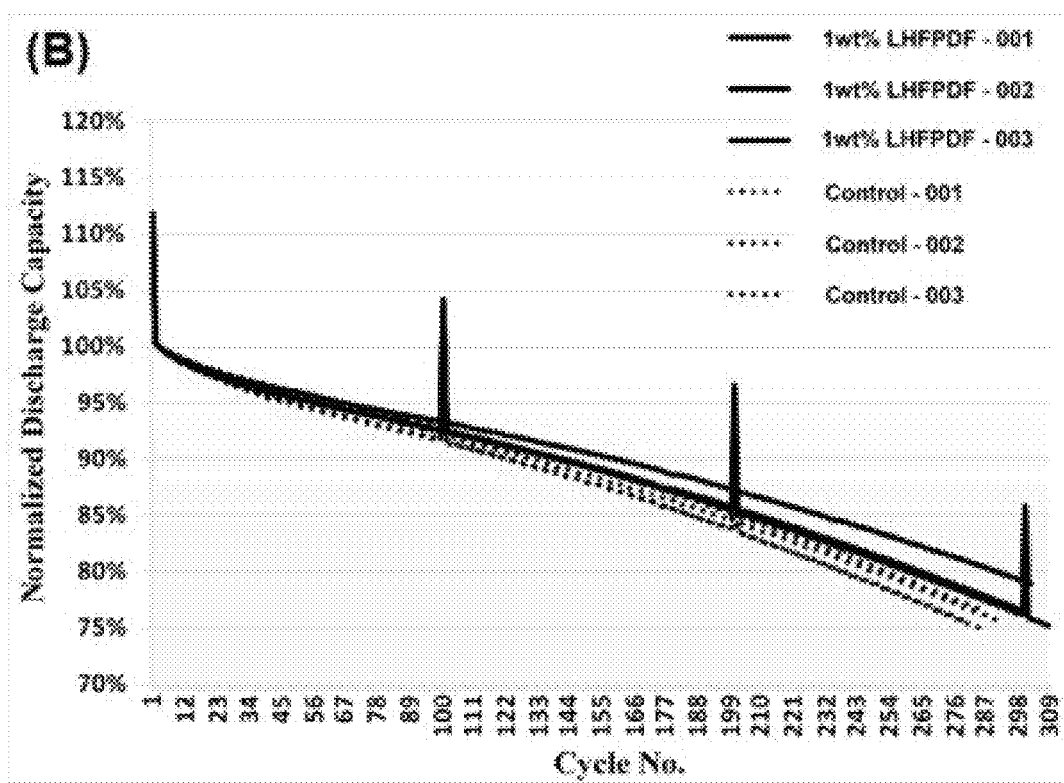

FIG. 5. Capacity retention (FIG. 5A) and Normalized capacity retention (FIG. 5B) of Si-dominant anode//NCM811 cathode coin full cells. The cathode used may be: (dotted line)—NCM811 Control, (solid line)—1 wt % Lithium 1,1,2,2,3,3-Hexafluoropropane-1,3-disulfonimide (LHFPDF)-containing NCM811. The electrolyte formulation used may be 1.2 M LiPF6 in FEC/EMC (3/7 wt %). The control cathodes contain about 92 wt % NCM811, 4 wt % Super P and 4 wt % PVDF5130, and may be coated on 15 μm Al foil. The average loading may be about 20-30 mg/cm². The 1 wt % LHFPDF-containing NCM811 cathodes contain about 91 wt % NCM811, 1 wt % LHFPDF, 4 wt % Super P and 4 wt % PVDF5130, and are also coated on 15 μm Al foil with a similar loading with control. The cells may be tested at 25° C.

The long-term cycling programs may include: (i) At the 1st cycle, Charge at 0.33 C to 4.2 V until 0.05 C, rest 5 minutes, discharge at 0.33 C to 3.1 V, rest 5 minutes; and (ii) from the 2nd cycle, Charge at 1 C to 4.2 V until 0.05 C, rest 5 minutes, discharge at 0.5 C to 3.1 V, rest 5 minutes. After every 100 cycles, the test conditions in the 1st cycle may be repeated.

FIG. 5 indicates the 1 wt % LHFPDF-containing NCM811 cathode-based coin full cells have better cycle performance than the control.

Figure 6:
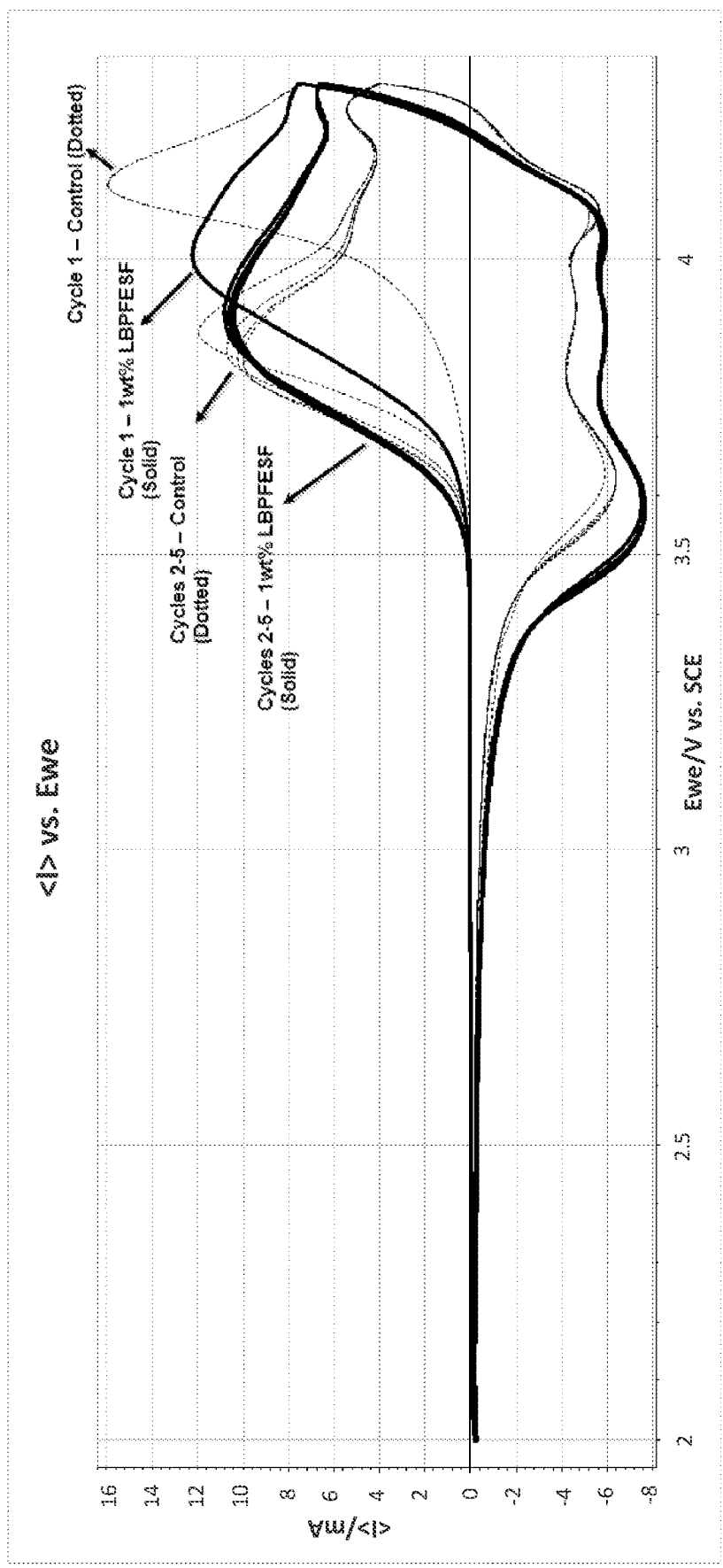
FIG. 6 shows cyclic voltammetry (CV) curves of NCM811 cathode-based coin half cells. The cathode used may be: (dotted line)—NCM811 Control, (solid line)—1 wt % Lithium Bis(pentafluoroethanesulfonyl)imide (LBPFESF)-containing NCM811, in accordance with an example embodiment of the disclosure.

FIG. 6. Cyclic voltammetry (CV) curves of NCM811 cathode-based coin half cells. The cathode used may be: (dotted line)—NCM811 Control, (solid line)—1 wt % Lithium Bis(pentafluoroethanesulfonyl)imide (LBPFESF)-containing NCM811. The electrolyte formulation used is 1.2 M LiPF$_6$ in FEC/EMC (3/7 wt %). The control cathodes contain about 92 wt % NCM811, 4 wt % Super P and 4 wt % PVDF5130, and may be coated on 15 μm Al foil. The average loading may be about 20-30 mg/cm². The 1 wt % LBPFESF-containing NCM811 cathodes contain about 91 wt % NCM811, 1 wt % LBPFESF, 4 wt % Super P and 4 wt % PVDF5130, and may be coated on 15 μm Al foil with a similar loading with control. The CV measurements may be carried out in the voltage range of 2-4.3 V at a scan rate of 0.2 mV s−1 using VMP3 equipment.

FIG. 6 shows that a clear oxidation peak appears at ~4.15 V (vs. Li/Li+) for the cell with NCM811 cathode (control) in the initial charge. This peak shifts to ~4.00 V (vs. Li/Li+) for the cell of 1 wt % LBPFESF-containing NCM811cathodes in the initial charge. In the following scanning cycles, the oxidation peak related voltage for NCM811 control cathode-based cells shifts to ~3.80 V (vs. Li/Li+); while the cell of 1 wt % LBPFESF-containing NCM811 cathodes becomes wide with the peak center at around 3.75V. In addition, with further scanning, there is an extra shoulder at around 3.85 V.

Figure 7A:
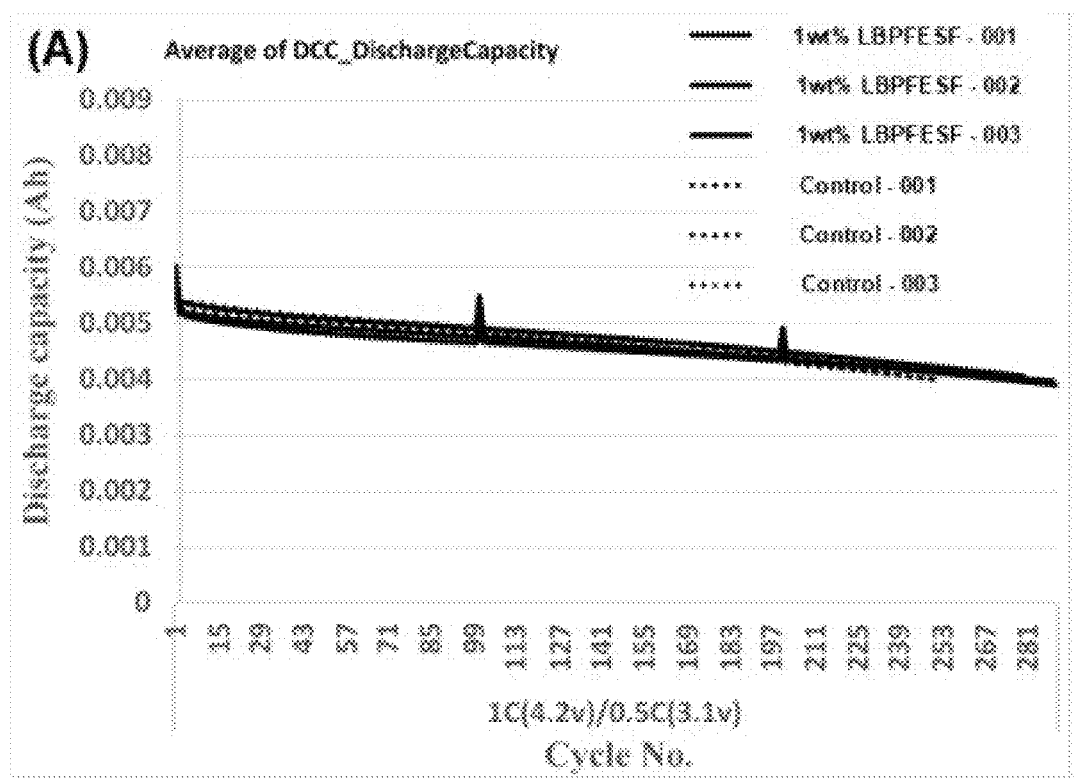
FIGS. 7A and 7B show the capacity retention (FIG. 7A) and normalized capacity retention (FIG. 7B) of Si-dominant anode//NCM811 cathode coin full cells. The cathode used may be: (dotted line)—NCM811 Control, (solid line)—1 wt % Lithium Bis(pentafluoroethanesulfonyl)imide (LBPFESF)-containing NCM811, in accordance with an example embodiment of the disclosure.
Figure 7B:
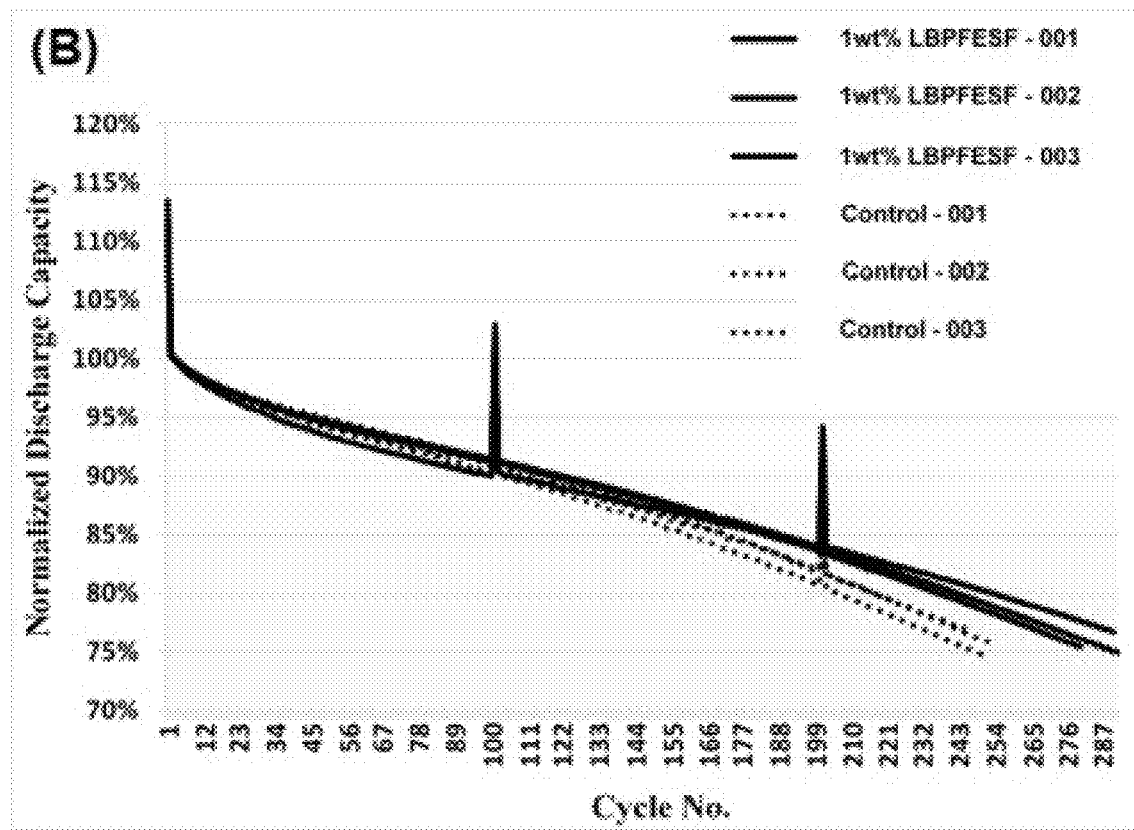

FIG. 7. Capacity retention (FIG. 7A) and Normalized capacity retention (FIG. 7B) of Si-dominant anode//NCM811 cathode coin full cells. The cathode used may be: (dotted line)—NCM811 Control, (solid line)—1 wt % Lithium Bis(pentafluoroethanesulfonyl)imide (LBPFESF)-containing NCM811. The electrolyte formulation used may be 1.2 M LiPF$_6$ in FEC/EMC (3/7 wt %). The control cathodes contain about 92 wt % NCM811, 4 wt % Super P and 4 wt % PVDF5130, and may be coated on 15 μm Al foil. The average loading may be about 20-30 mg/cm². The 1 wt % LBPFESF-containing NCM811 cathodes contain about 91 wt % NCM811, 1 wt % LBPFESF, 4 wt % Super P and 4 wt % PVDF5130, and may be coated on 15 μm Al foil with a similar loading with control. The cells may be tested at 25° C.

The long-term cycling programs may be as in FIG. 5.

FIG. 7 indicates the 1 wt % LBPFESF-containing cathode-based coin full cells have better cycle performance than the control.

Figure 8:
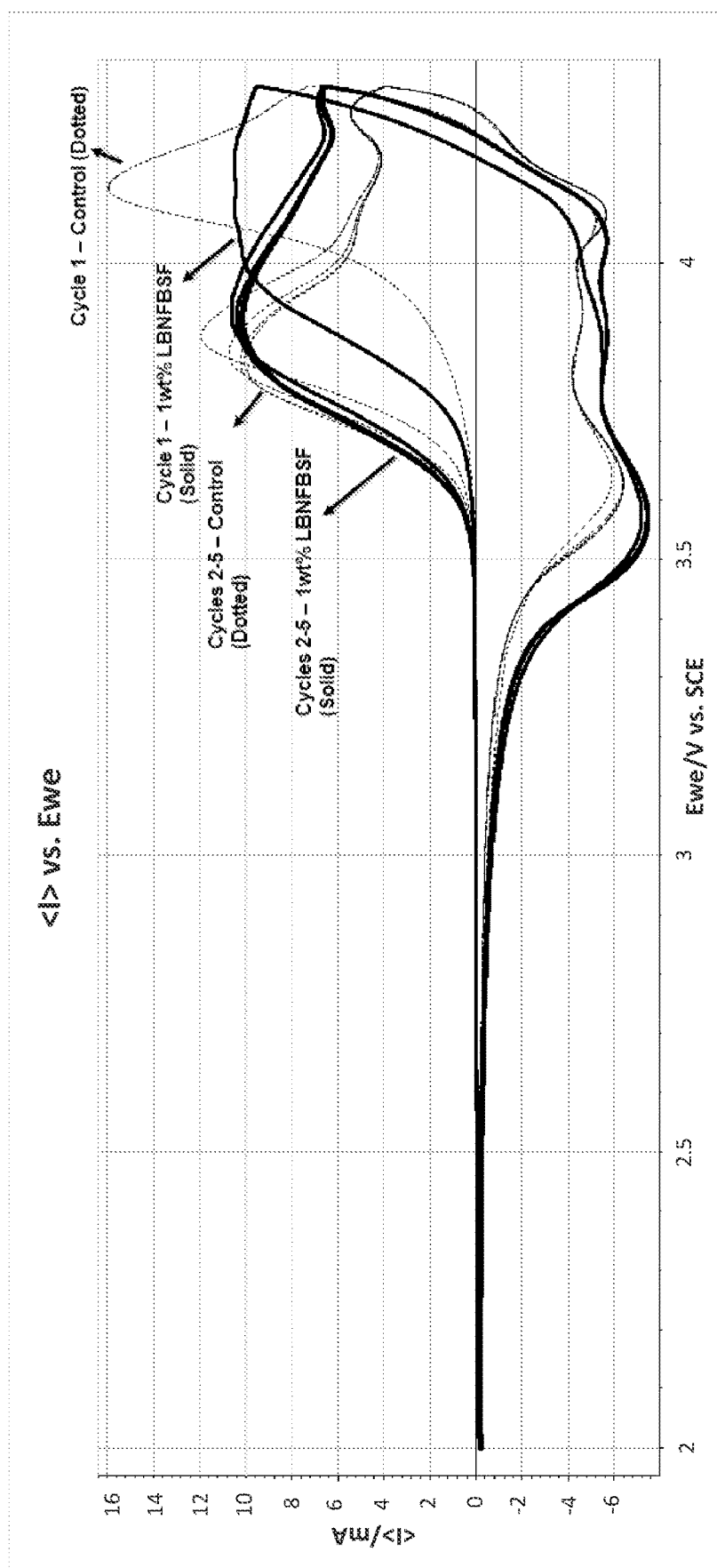
FIG. 8 shows cyclic voltammetry (CV) curves of NCM811 cathode-based coin half cells. The cathode used may be: (dotted line)—NCM811 Control, (solid line)—1 wt % Lithium Bis(nonafluorobutanesulfonyl)imide (LBNFBSF)-containing NCM811, in accordance with an example embodiment of the disclosure.

FIG. 8. Cyclic voltammetry (CV) curves of NCM811 cathode-based coin half cells. The cathode used may be: (dotted line)—NCM811 Control, (solid line)—1 wt % Lithium Bis(nonafluorobutanesulfonyl)imide (LBNFBSF)-containing NCM811. The electrolyte formulation used may be 1.2 M LiPF6 in FEC/EMC (3/7 wt %). The control cathodes contain about 92 wt % NCM811, 4 wt % Super P and 4 wt % PVDF5130, and may be coated on 15 μm Al foil. The average loading may be about 20-30 mg/cm². The 1 wt % LBNFBSF-containing NCM811 cathodes contain about 91 wt % NCM811, 1 wt % LBNFBSF, 4 wt % Super P and 4 wt % PVDF5130, and may be coated on 15 μm Al foil with a similar loading with control. The CV measurements may be carried out in the voltage range of 2-4.3 V at a scan rate of 0.2 mV s−1 using VMP3 equipment.

FIG. 8 shows that a clear oxidation peak appears at ~4.15 V (vs. Li/Li+) for the cell with NCM811 cathode (control) in the initial charge. This peak shifts to ~4.00 V (vs. Li/Li+) for the cell of 1 wt % LBNFBSF-containing NCM811cathodes in the initial charge. In the following scanning cycles, the oxidation peak related voltage for NCM811 control cathode-based cells shifts to ~3.80 V (vs. Li/Li+); while the cell of 1 wt % LBNFBSF-containing NCM811 cathodes becomes wide with the peak center at around 3.75V. In addition, with further scanning, there is an extra shoulder at around 3.85 V.

Figure 9A:
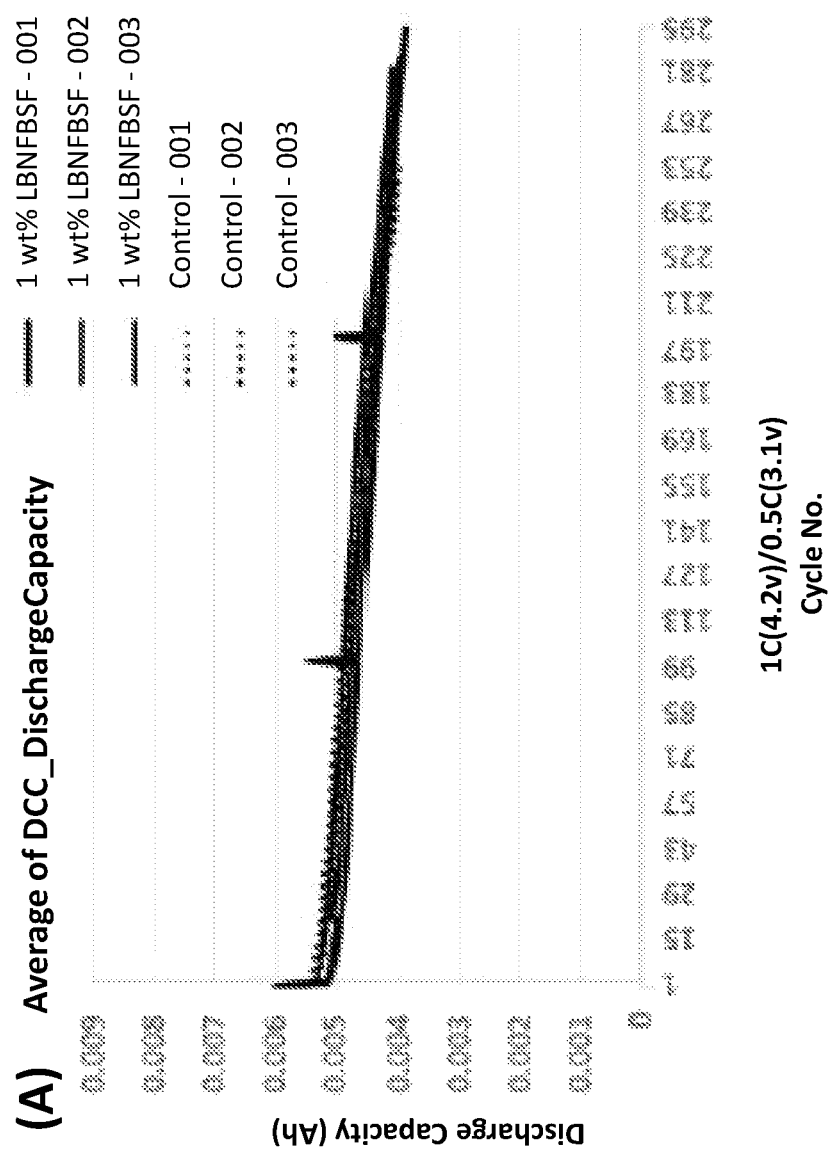
FIGS. 9A and 9B show the capacity retention (FIG. 9A) and normalized capacity retention (FIG. 9B) of Si-dominant anode//NCM811 cathode coin full cells. The cathodes used may be: (dotted line)—NCM811 Control, (solid line)—1 wt % Lithium Bis(nonafluorobutanesulfonyl)imide (LBNFBSF)-containing NCM811, in accordance with an example embodiment of the disclosure.
Figure 9B:
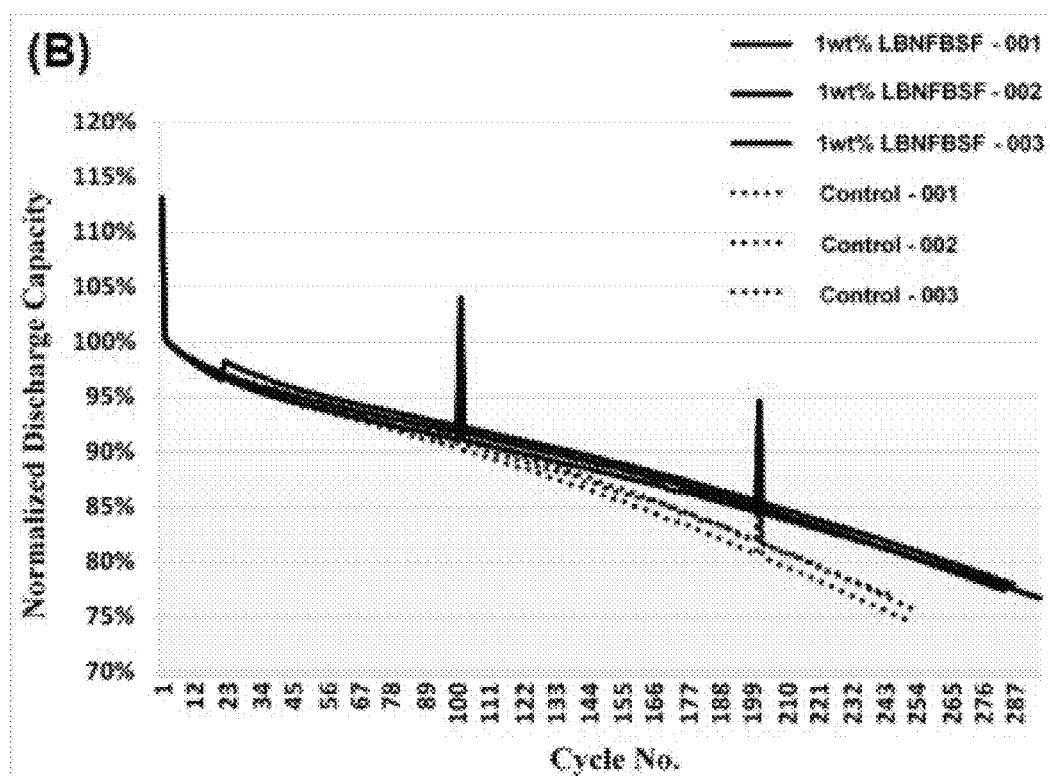

FIG. 9. Capacity retention (FIG. 9A) and Normalized capacity retention (FIG. 9B) of Si-dominant anode//NCM811 cathode coin full cells. The cathodes used may be: (dotted line)—NCM811 Control, (solid line)—1 wt % Lithium Bis(nonafluorobutanesulfonyl)imide (LBNFBSF)-containing NCM811. The electrolyte formulation used is 1.2 M LiPF6 in FEC/EMC (3/7 wt %). The control cathodes contain about 92 wt % NCM811, 4 wt % Super P and 4 wt % PVDF5130, and may be coated on 15 μm Al foil. The average loading may be about 20-30 mg/cm2. The 1 wt % LBNFBSF-containing NCM811 cathodes contain about 91 wt % NCM811, 1 wt % LBNFBSF, 4 wt % Super P and 4 wt % PVDF5130, and may be coated on 15 μm Al foil with a similar loading with control. The cells may be tested at 25° C.

The long-term cycling programs may be as in FIG. 5.

FIG. 9 indicates the 1 wt % LBNFBSF-containing cathode-based coin full cells have better cycle performance than the control.

Figure 10A:
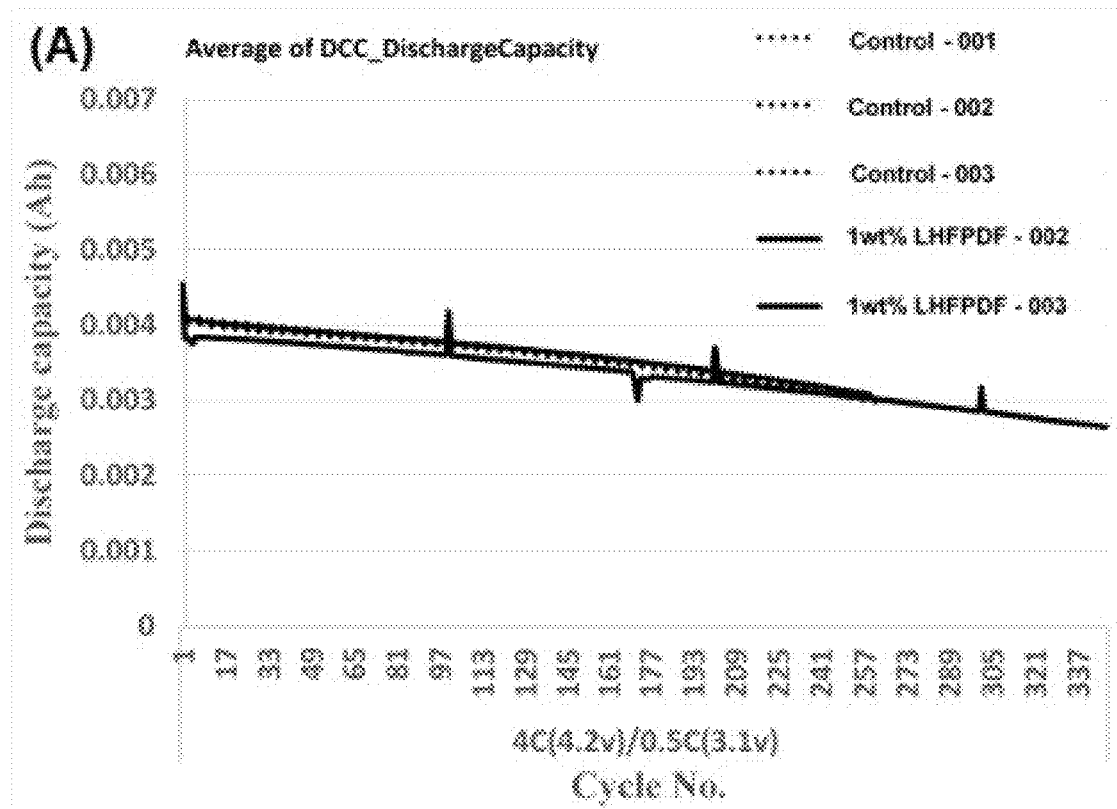
FIGS. 10A and 10B show the capacity retention (FIG. 10A) and normalized capacity retention (FIG. 10B) of Si-dominant anode//NCM811 cathode coin full cells. The electrolytes used may be: (dotted line) 1.2 M $LiPF_6$ in FEC/EMC (3/7 wt %)—Control, (thick solid line) 1.2 M $LiPF_6$ in FEC/EMC (3/7 wt %)+1 wt % Lithium 1,1,2,2,3,3-Hexafluoropropane-1,3-disulfonimide (LHFPDF), in accordance with an example embodiment of the disclosure.
Figure 10B:
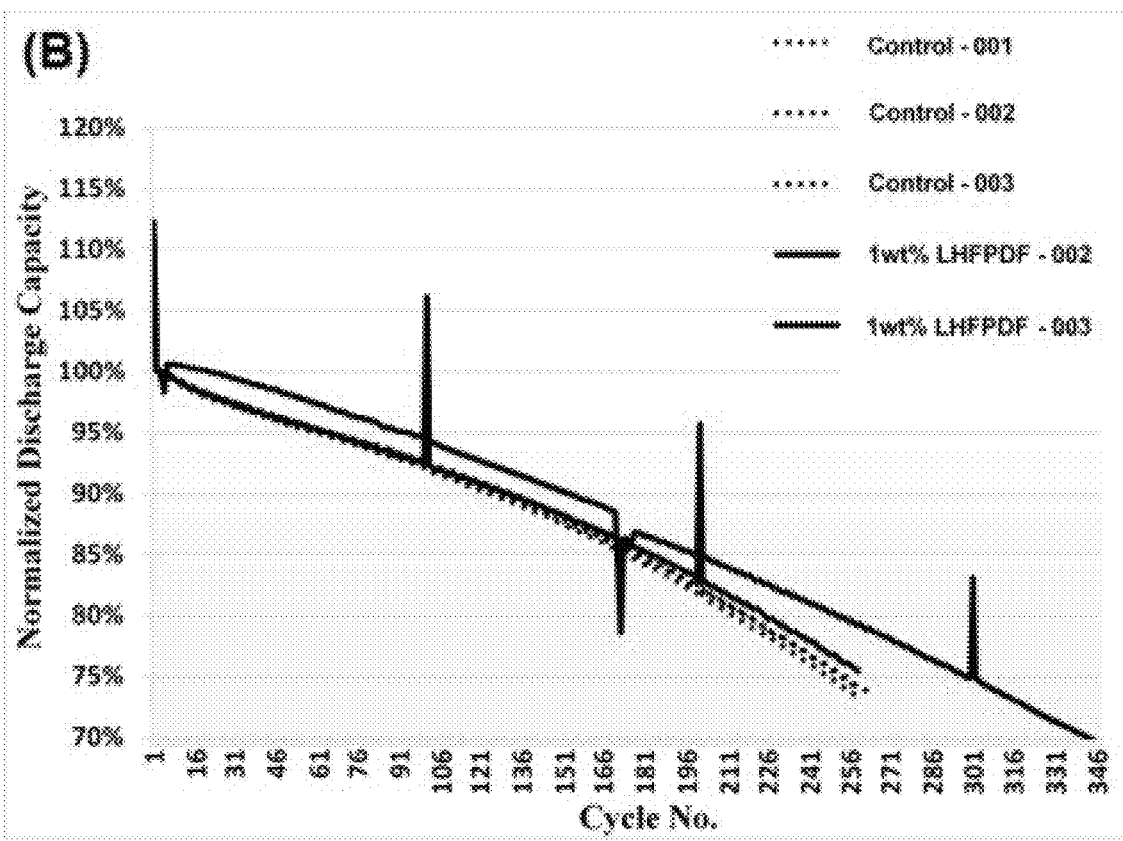

FIG. 10. Capacity retention (FIG. 10A) and Normalized capacity retention (FIG. 10B) of Si-dominant anode//NCM811 cathode coin full cells. The electrolytes used may be: (dotted line) 1.2 M LiPF$_6$ in FEC/EMC (3/7 wt %)—Control, (thick solid line) 1.2 M LiPF$_6$ in FEC/EMC (3/7 wt %)+1 wt % Lithium 1,1,2,2,3,3-Hexafluoropropane-1,3-disulfonimide (LHFPDF). The Si-dominant anodes contain about 80 wt % Si, 5 wt % graphite and 15 wt % glassy carbon (from resin) and may be laminated on 15 μm Cu foil. The average loading may be about 2-5 mg/cm2. The cathodes contain about 92 wt % NCM811, 4 wt % Super P and 4 wt % PVDF5130, and may be coated on 15 μm Al foil. The average loading is about 20-30 mg/cm2. The cells may be tested at 25° C.

The long-term cycling program for both control and the 1 wt % LHFPDF-containing electrolyte-based coin full cells may include: (i) At the 1 st cycle, Charge at 0.33 C to 4.2 V until 0.05 C, rest 5 minutes, discharge at 0.33 C to 3.1 V, rest 5 minutes; and (ii) from the 2nd cycle, Charge at 4 C to 4.2 V until 0.05 C, rest 5 minutes, discharge at 0.5 C to 3.1 V, rest 5 minutes. After every 100 cycles, the test conditions in the 1st cycle may be repeated.

FIG. 10 indicates that 1 wt % LHFPDF-containing electrolyte-based coin full cells have similar cycle performance with reference electrolyte-based control cells when tested with 4 C(4.2V)/0.5 C(3.1 V) at 25° C.

Figure 11A:
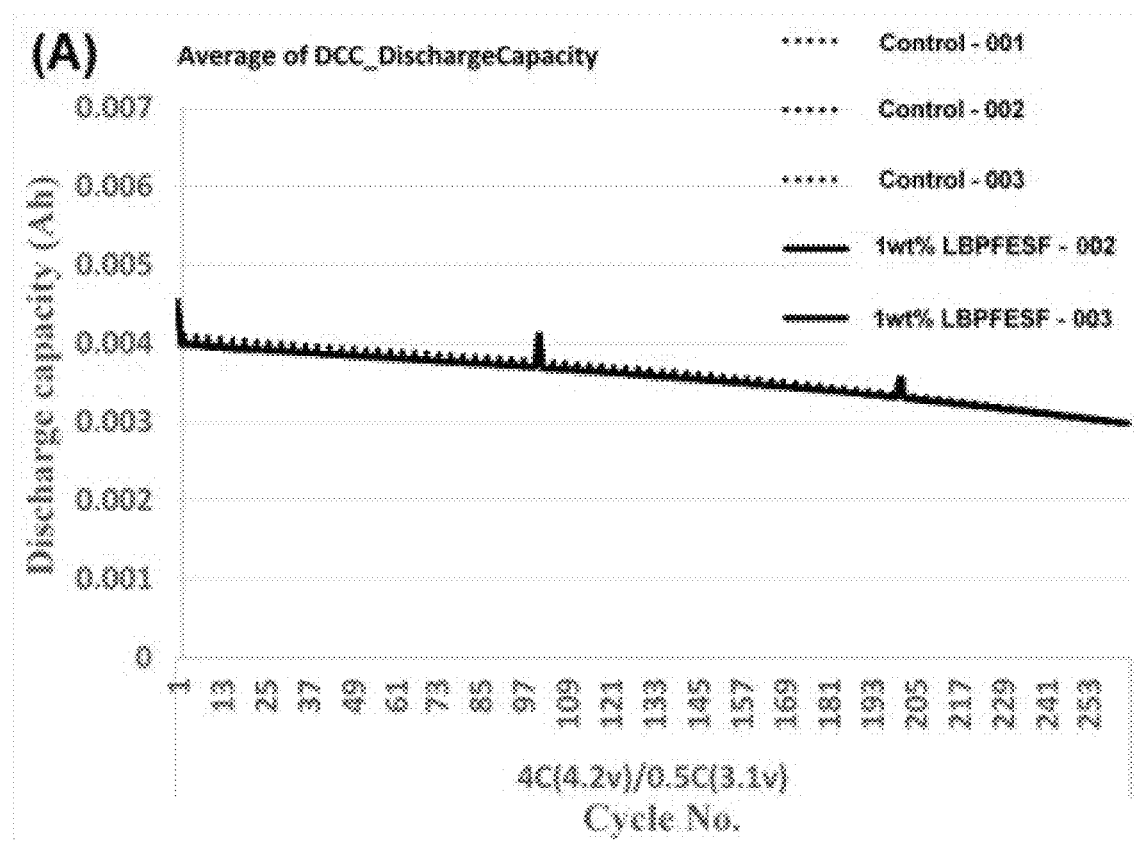
FIGS. 11A and 11B show the capacity retention (FIG. 11A) and normalized capacity retention (FIG. 11B) of Si-dominant anode//NCM811 cathode coin full cells. The electrolytes used may be: (dotted line) 1.2 M $LiPF_6$ in FEC/EMC (3/7 wt %)—Control, (thick solid line) 1.2 M $LiPF_6$ in FEC/EMC (3/7 wt %)+1 wt % Lithium Bis(pentafluoroethanesulfonyl)imide (LBPFESF), in accordance with an example embodiment of the disclosure.
Figure 11B:
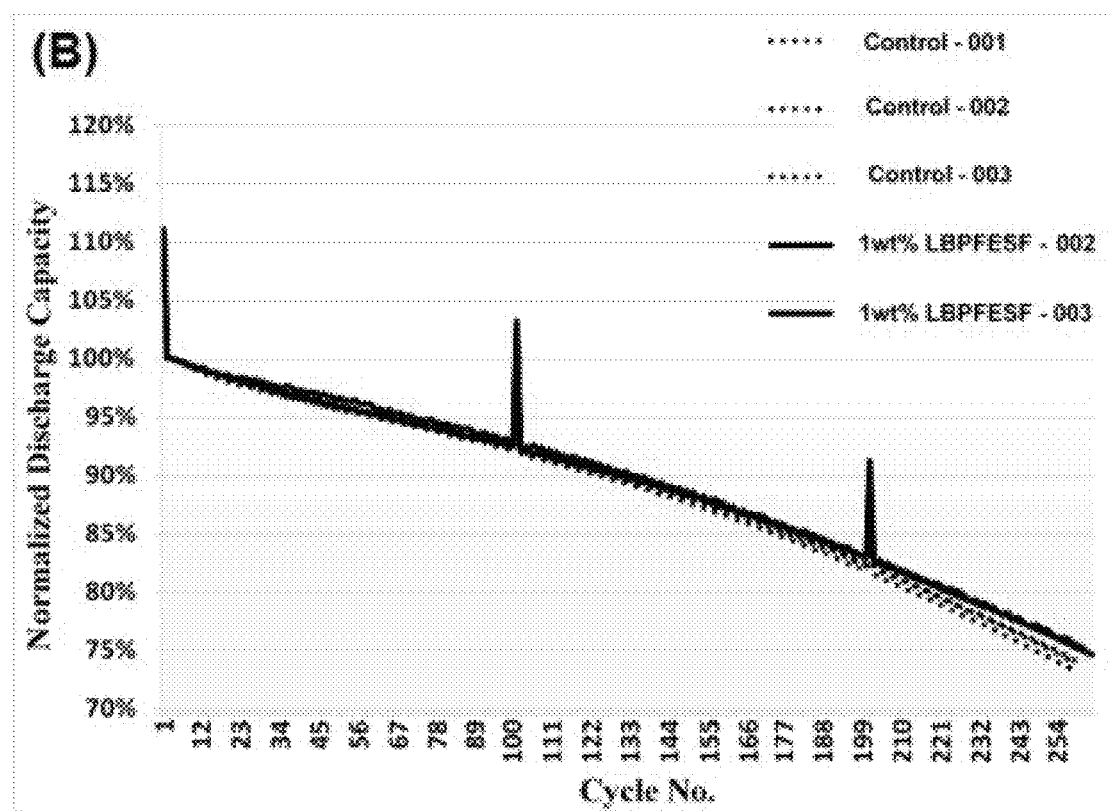

FIG. 11. Capacity retention (FIG. 11A) and Normalized capacity retention (FIG. 11B) of Si-dominant anode//NCM811 cathode coin full cells. The electrolytes used may be: (dotted line) 1.2 M LiPF$_6$ in FEC/EMC (3/7 wt %)—Control, (thick solid line) 1.2 M LiPF$_6$ in FEC/EMC (3/7 wt %)+1 wt % Lithium Bis(pentafluoroethanesulfonyl) imide (LBPFESF). The Si-dominant anodes contain about 80 wt % Si, 5 wt % graphite and 15 wt % glassy carbon (from resin) and may be laminated on 15 μm Cu foil. The average loading may be about 2-5 mg/cm$^2$. The cathodes contain about 92 wt % NCM811, 4 wt % Super P and 4 wt % PVDF5130, and may be coated on 15 μm Al foil. The average loading may be about 20-30 mg/cm$^2$. The cells may be tested at 25° C.

The long-term cycling program for both control and the 1 wt % LBPFESF-containing electrolyte-based coin full may be the same as shown in FIG. 10.

FIG. 11 shows that 1 wt % LBPFESF-containing electrolyte-based coin full cells have similar cycle performance with reference electrolyte-based control cells when tested with 4 C(4.2V)/0.5 C(3.1V) at 25° C.

Figure 12A:
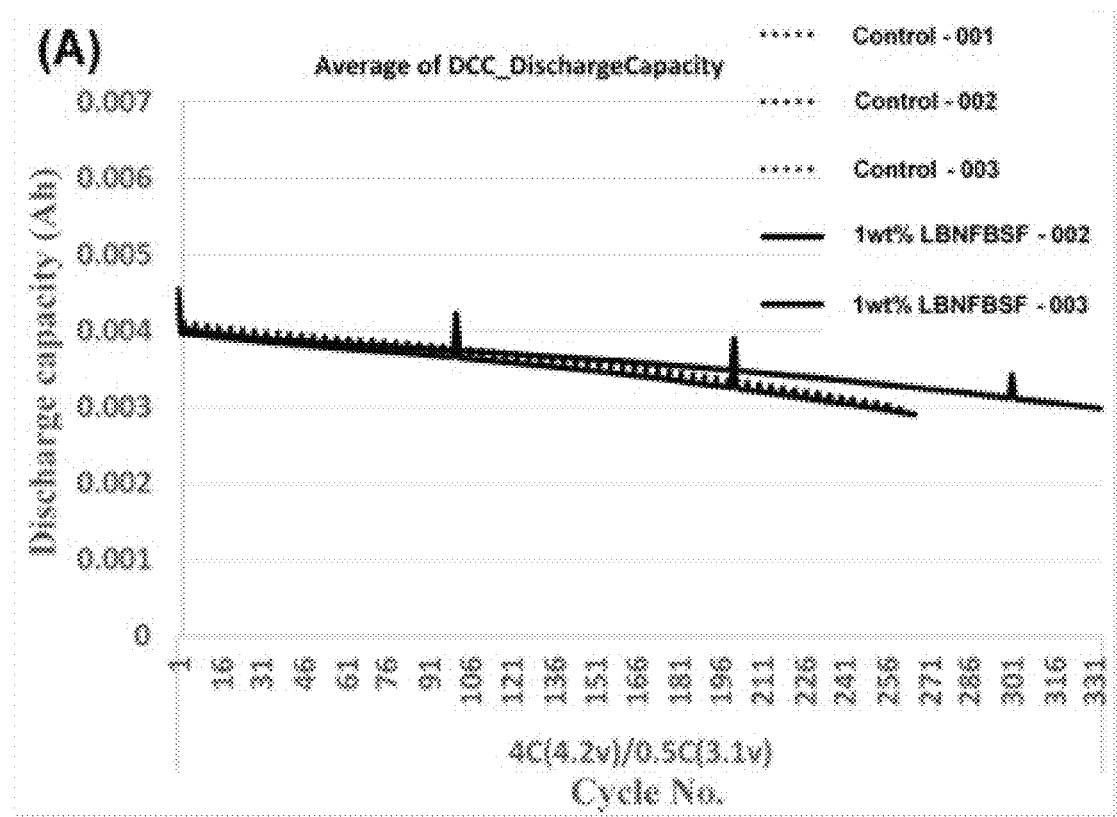
FIGS. 12A and 12B show the capacity retention (FIG. 12A) and normalized capacity retention (FIG. 12B) of Si-dominant anode//NCM811 cathode coin full cells. The electrolytes used may be: (dotted line) 1.2 M $LiPF_6$ in FEC/EMC (3/7 wt %)—Control, (thick solid line) 1.2 M $LiPF_6$ in FEC/EMC (3/7 wt %)+1 wt % Lithium Bis(nonafluorobutanesulfonyl)imide (LBNFBSF), in accordance with an example embodiment of the disclosure.
Figure 12B:
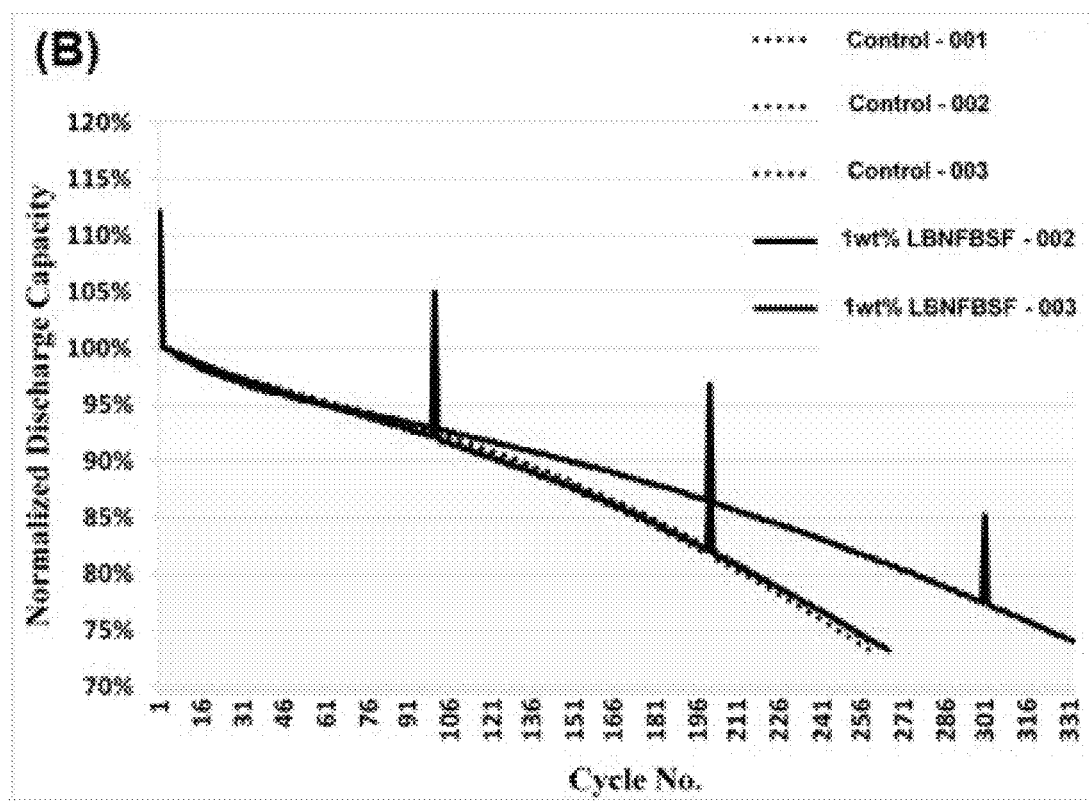

FIG. 12. Capacity retention (FIG. 12A) and Normalized capacity retention (FIG. 12B) of Si-dominant anode// NCM811 cathode coin full cells. The electrolytes used may be: (dotted line) 1.2 M LiPF$_6$ in FEC/EMC (3/7 wt %)—Control, (thick solid line) 1.2 M LiPF$_6$ in FEC/EMC (3/7 wt %)+1 wt % Lithium Bis(nonafluorobutanesulfonyl) imide (LBNFBSF). The Si-dominant anodes contain about 80 wt % Si, 5 wt % graphite and 15 wt % glassy carbon (from resin) and may be laminated on 15 μm Cu foil. The average loading may be about 2-5 mg/cm$^2$. The cathodes contain about 92 wt % NCM811, 4 wt % Super P and 4 wt % PVDF5130, and may be coated on 15 μm Al foil. The average loading may be about 20-30 mg/cm$^2$. These cells may be tested at 25° C.

The long-term cycling program for both control and the 1 wt % LBNFBSF-containing electrolyte-based coin full are the same as shown in FIG. 10.

FIG. 12 shows that 1 wt % LBNFBSF-containing electrolyte-based coin full cells have similar cycle performance with reference electrolyte-based control cells when tested with 4 C(4.2V)/0.5 C(3.1V) at 25° C.

Various embodiments have been described above. Although the invention has been described with reference to these specific embodiments, the descriptions are intended to be illustrative and are not intended to be limiting. Various modifications and applications may occur to those skilled in the art without departing from the true spirit and scope of the invention as defined in the appended claims.

What is claimed is:

1. An energy storage device comprising:
   an anode and a cathode, where at least one of the anode or the cathode contains an electrode additive;
   a separator between the anode and the cathode; and
   an electrolyte composition; wherein
   said electrode additive comprises an asymmetrical alkylsulfonyl imide or alkylene sulfonylimide salt; and
   wherein the electrode additive is of formula (Ia) or (Ib):

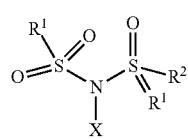

(Ia)

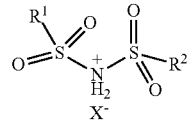

(Ib)

wherein X is Na, K, Rb, Cs, Fr, Mg, Ca, Zn or Al;
R$^1$ and R$^2$ are different and are selected from the group consisting of H, OH, alkylene, alkoxy, alkenyl, alkenylene, alkynyl, alkynylene, cycloalkyl, cycloalkylene, aryl, arylene, heteroaryl, heteroalkyl, heteroalkylene, heterocycloalkyl, and heterocycloalkylene, which may be also further optionally substituted.

2. The energy storage device of claim 1, wherein the anode is a Si-dominant electrode.

3. The energy storage device of claim 1, wherein the electrode additive comprises an asymmetrical perfluoroalkylsulfonyl imide or acyclic perfluoroalkylene sulfonylimide salt.

4. The energy storage device of claim 1, wherein the electrode additive is Potassium (trifluoromethanesulfonyl) (vinylsulfonyl)imide.

5. An energy storage device comprising:
   a first electrode and a second electrode, wherein at least one of the first electrode and the second electrode is a Si-based electrode;
   a separator between the first electrode and the second electrode; and
   an electrolyte composition; wherein
   said electrolyte composition comprises at least one electrolyte additive comprising an asymmetrical alkylsulfonyl imide or alkylene sulfonylimide salt; and
   wherein the electrolyte additive is of formula (Ia) or (Ib):

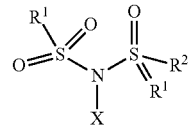

(Ia)

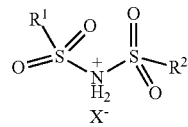

(Ib)

wherein X is Na, K, Rb, Cs, Fr, Mg, Ca, Zn or Al;
R$^1$ and R$^2$ are different and are selected from the group consisting of H, OH, alkylene, alkoxy, alkenyl, alkenylene, alkynyl, alkynylene, cycloalkyl, cycloalkylene, aryl, arylene, heteroaryl, heteroalkyl, heteroalkylene, heterocycloalkyl, and heterocycloalkylene, which may be also further optionally substituted.

6. The energy storage device of claim 5, wherein the second electrode is a Si-dominant electrode.

7. The energy storage device of claim 5, wherein the second electrode comprises a self-supporting composite material film.

8. The energy storage device of claim 7, wherein the composite material film comprises:
greater than 0% and less than about 95% by weight of silicon particles, and
greater than 0% and less than about 90% by weight of one or more types of carbon phases, wherein at least one of the one or more types of carbon phases is a substantially continuous phase that holds the composite material film together such that the silicon particles are distributed throughout the composite material film.

9. The energy storage device of claim 5, wherein the electrolyte additive comprises an asymmetrical perfluoroalkylsulfonyl imide or acyclic perfluoroalkylene sulfonylimide salt.

10. The energy storage device of claim 5, wherein the electrolyte additive is Potassium (trifluoromethanesulfonyl)(vinylsulfonyl)imide.

11. The energy storage device of claim 1, wherein the electrolyte composition comprises a solvent selected from the group consisting of one or more of ethyl methyl carbonate (EMC), methyl acetate, dimethyl carbonate (DMC), diethyl carbonate (DEC), gamma butyrolactone, methyl acetate (MA), ethyl acetate (EA), methyl propanoate, fluoro ethylene carbonate (FEC), di-fluoroethylene carbonate (DiFEC), Trifluoropropylene carbonate (TFPC), ethylene carbonate (EC), vinylene carbonate (VC) and propylene carbonate (PC).

12. The energy storage device of claim 11, wherein the solvent comprises FEC, EC or TFPC at a concentration of at 5% or more.

13. The energy storage device of claim 12, wherein the electrolyte composition is substantially free of non-fluorine containing cyclic carbonates.

14. A method of forming an energy storage device, the method comprising:
forming an energy storage device comprising a cathode, an electrolyte composition, and an anode;
wherein said one or more of said cathode or said anode and/or said electrolyte composition comprise an additive compound;
said additive compound comprising an asymmetrical alkylsulfonyl imide or alkylene sulfonylimide salt;
wherein said one or both of said cathode and said anode is formed using, at least, the following steps:
said electrode material is mixed to create a slurry;
said electrolyte composition is added to said slurry;
said slurry is coated on metal foil; and
the coated metal foil is dried salt; and
wherein the additive compound is of formula (Ia) or (Ib):

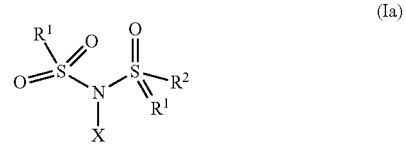
(Ia)

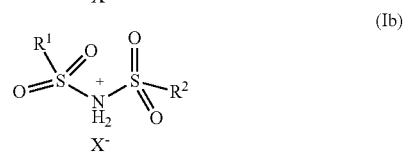
(Ib)

wherein X is Na, K, Rb, Cs, Fr, Mg, Ca, Zn or Al;
$R^1$ and $R^2$ are different and are selected from the group consisting of H, OH, alkylene, alkoxy, alkenyl, alkenylene, alkynyl, alkynylene, cycloalkyl, cycloalkylene, aryl, arylene, heteroaryl, heteroalkyl, heteroalkylene, heterocycloalkyl, and heterocycloalkylene, which may be also further optionally substituted.

15. The method of claim 14, wherein the anode is a Si-dominant electrode.

16. The method of claim 14, wherein the anode comprises a self-supporting composite material film.

17. The method of claim 16, wherein the composite material film comprises:
greater than 0% and less than about 95% by weight of silicon particles, and
greater than 0% and less than about 90% by weight of one or more types of carbon phases, wherein at least one of the one or more types of carbon phases is a substantially continuous phase that holds the composite material film together such that the silicon particles are distributed throughout the composite material film.

18. The method of claim 14, wherein the additive compound comprises a symmetrical or asymmetrical perfluoroalkylsulfonyl imide or acyclic perfluoroalkylene sulfonylimide salt.

19. The method of claim 14, wherein the additive compound is Potassium (trifluoromethanesulfonyl)(vinylsulfonyl)imide.

* * * * *